United States Patent
Reiley

(10) Patent No.: US 6,949,123 B2
(45) Date of Patent: Sep. 27, 2005

(54) FACET ARTHROPLASTY DEVICES AND METHODS

(75) Inventor: Mark A Reiley, Piedmont, CA (US)

(73) Assignee: Archus Orthopedics Inc., Redmond, WA (US)

( * ) Notice: Subject to any disclaimer, the term of this patent is extended or adjusted under 35 U.S.C. 154(b) by 10 days.

(21) Appl. No.: 10/657,844

(22) Filed: Sep. 9, 2003

(65) Prior Publication Data

US 2004/0049272 A1 Mar. 11, 2004

Related U.S. Application Data

(62) Division of application No. 10/615,727, filed on Jul. 9, 2003, which is a division of application No. 09/693,272, filed on Oct. 20, 2000, now Pat. No. 6,610,091.
(60) Provisional application No. 60/160,891, filed on Oct. 22, 1999.

(51) Int. Cl.[7] .............. A61F 2/28; A61F 17/70; A61F 17/80
(52) U.S. Cl. .............. 623/17.11; 606/60; 606/61; 606/69; 606/70; 606/71
(58) Field of Search .............. 606/60–74; 623/17.11–16

(56) References Cited

U.S. PATENT DOCUMENTS

| | | |
|---|---|---|
| 5,015,255 A | 5/1991 | Kuslich |
| 5,092,866 A | 3/1992 | Breard et al. |
| 5,258,031 A | 11/1993 | Salib et al. |
| 5,300,073 A | 4/1994 | Ray et al. |
| 5,415,661 A | 5/1995 | Holmes |
| 5,425,773 A | 6/1995 | Boyd et al. |
| 5,445,639 A | 8/1995 | Kuslich et al. |
| 5,491,882 A | 2/1996 | Walston et al. |
| 5,507,823 A | 4/1996 | Walston et al. |
| 5,527,312 A | 6/1996 | Ray |
| 5,562,738 A | 10/1996 | Boyd et al. |
| 5,571,191 A | 11/1996 | Fitz |
| 5,577,995 A | 11/1996 | Walker et al. |
| 5,602,845 A | 2/1997 | Wahl |
| 5,603,713 A | 2/1997 | Aust et al. |
| 5,741,261 A | 4/1998 | Moskovitz et al. |
| 5,836,948 A | 11/1998 | Zucherman et al. |
| 5,860,977 A | 1/1999 | Zucherman et al. |
| 5,879,396 A | 3/1999 | Walston et al. |
| RE36,221 E | 6/1999 | Breard et al. |

(Continued)

FOREIGN PATENT DOCUMENTS

| | | |
|---|---|---|
| IE | S970323 | 6/1998 |
| WO | WO 95/05783 A1 | 3/1995 |
| WO | WO 96/00049 | 1/1996 |
| WO | WO 98/56301 A1 | 12/1998 |
| WO | WO 99/05995 A1 | 2/1999 |
| WO | WO 99/60957 A1 | 12/1999 |
| WO | WO 99/65412 A1 | 12/1999 |
| WO | WO 00/62684 A1 | 10/2000 |
| WO | WO 01/97721 A2 | 12/2001 |
| WO | WO 02/089712 A1 | 11/2002 |
| WO | WO 03/020143 A1 | 3/2003 |

*Primary Examiner*—David J. Isabella
(74) *Attorney, Agent, or Firm*—Wilson, Sonsini, Goodrich & Rosati

(57) ABSTRACT

A prosthesis assembly replaces all or a portion of a caudal portion of a left natural facet joint (i.e., a left superior articular process) and all or a portion of a caudal portion of a right natural facet joint (i.e., a right superior articular process) on a vertebral body. The prosthesis assembly has a left prosthesis body accommodating fixation to the vertebral body at or near a left pedicle and without support by a lamina. An artificial left facet joint structure is carried by the left prosthesis body and is adapted and configured to replace all or a portion of a caudal portion of the left natural facet joint. The prosthesis assembly also has a right prosthesis body accommodating fixation to the vertebral body at or near a right pedicle and without support by a lamina. An artificial right facet joint structure is carried by the right prosthesis body and is adapted and configured to replace all or a portion of a caudal portion of the left natural facet joint.

56 Claims, 17 Drawing Sheets

U.S. PATENT DOCUMENTS

| | | |
|---|---|---|
| 6,048,342 A | 4/2000 | Zucherman et al. |
| 6,068,630 A | 5/2000 | Zucherman et al. |
| RE36,758 E | 6/2000 | Fitz |
| 6,132,464 A | 10/2000 | Martin |
| 6,200,322 B1 | 3/2001 | Branch et al. |
| 6,293,949 B1 | 9/2001 | Justis et al. |
| 6,419,703 B1 | 7/2002 | Fallin et al. |
| 6,565,605 B2 | 5/2003 | Goble et al. |
| 6,579,319 B2 | 6/2003 | Goble et al. |
| 6,610,091 B1 | 8/2003 | Reiley |
| 6,669,729 B2 | 12/2003 | Chin |
| 6,761,720 B1 | 7/2004 | Senegas |
| 6,783,527 B2 | 8/2004 | Drewry et al. |
| 2001/0012938 A1 | 8/2001 | Zucherman et al. |
| 2001/0020170 A1 | 9/2001 | Zucherman et al. |
| 2002/0029038 A1 | 3/2002 | Zucherman et al. |
| 2002/0151895 A1 | 10/2002 | Soboleski et al. |
| 2004/0116927 A1 | 6/2004 | Graf |
| 2004/0127989 A1 | 7/2004 | Dooris et al. |
| 2004/0143264 A1 | 7/2004 | McAfee |

TRIMMING OF SUPERIOR FACET TO DECOMPRESS NERVE ROOT PRIOR TO REAMING (S1 IN THIS CASE)

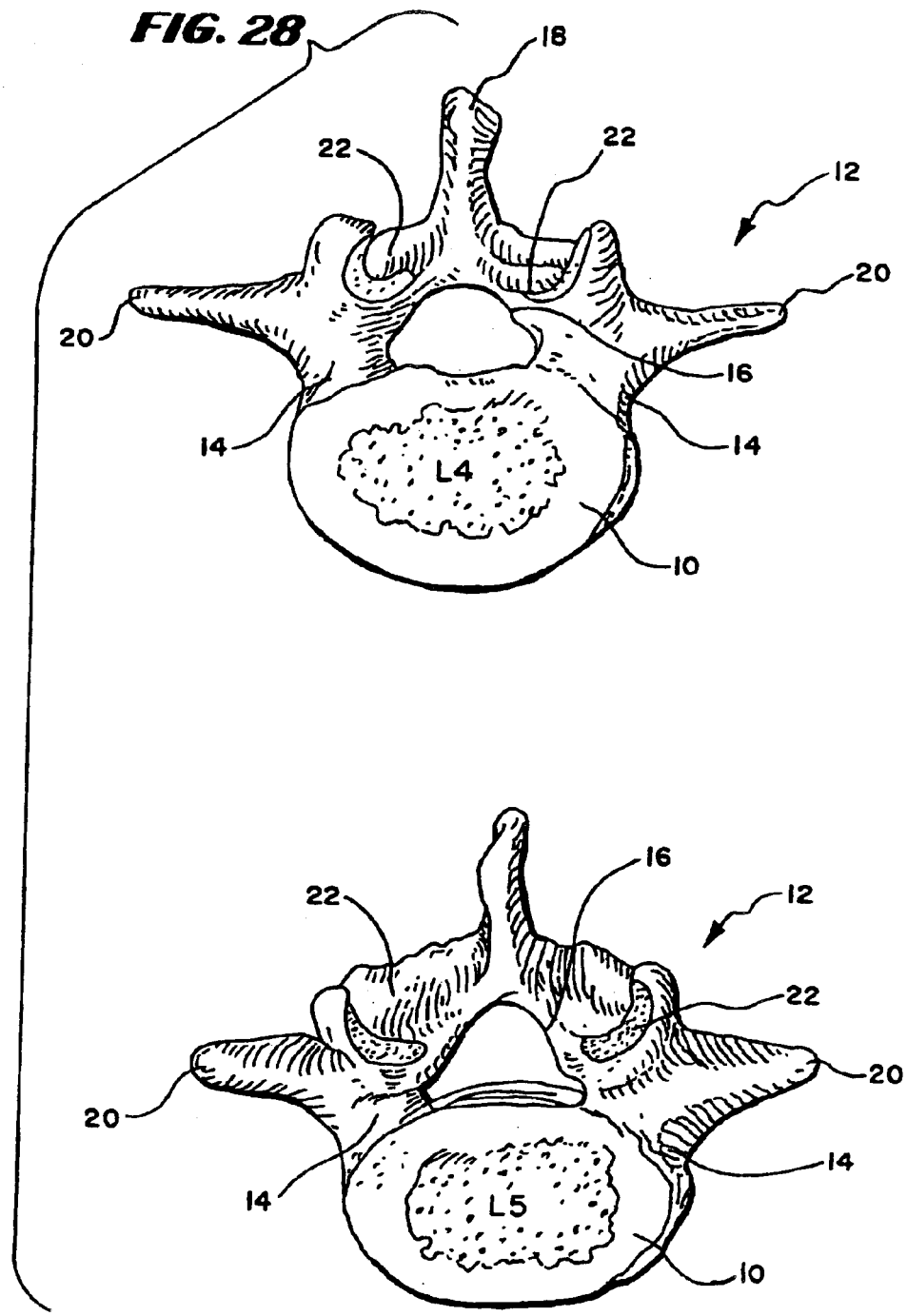

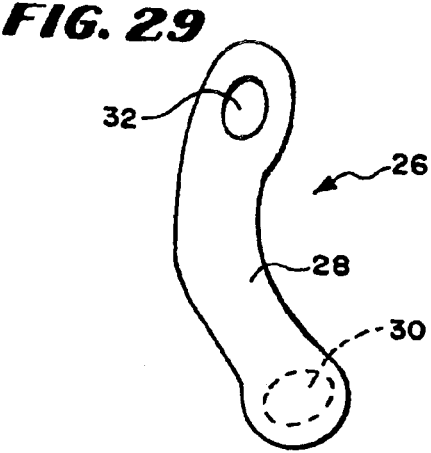
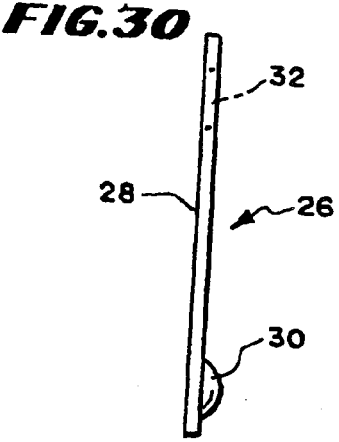
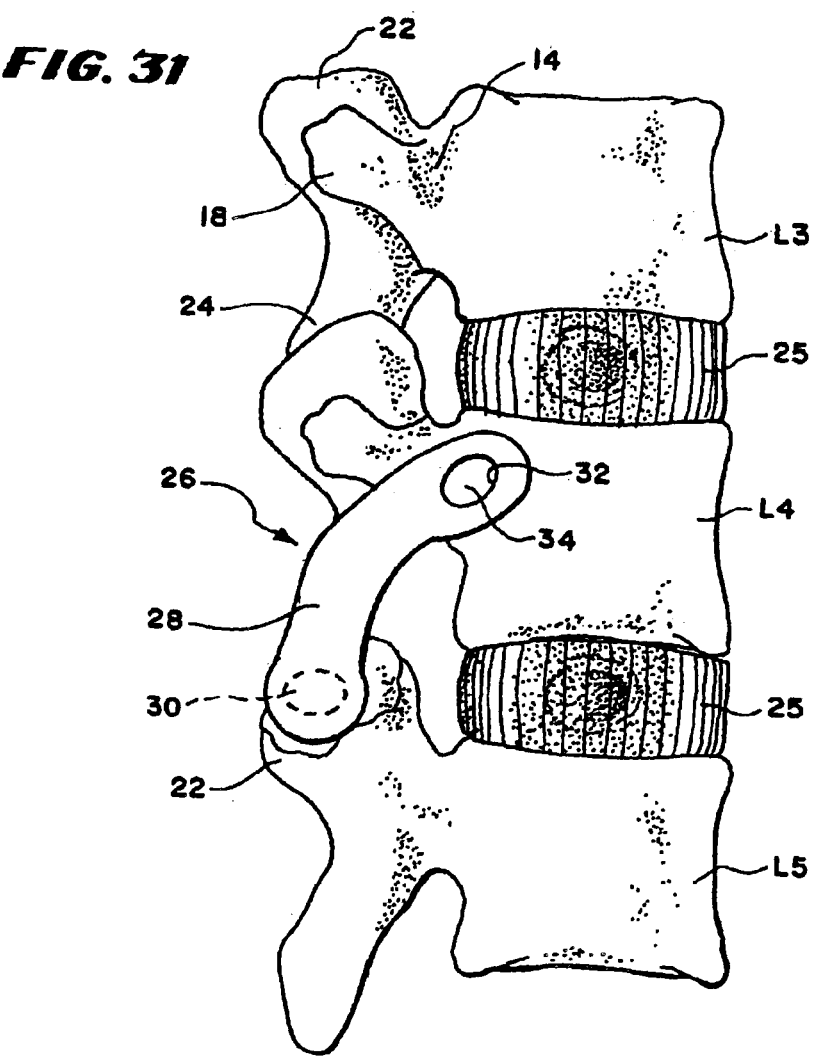

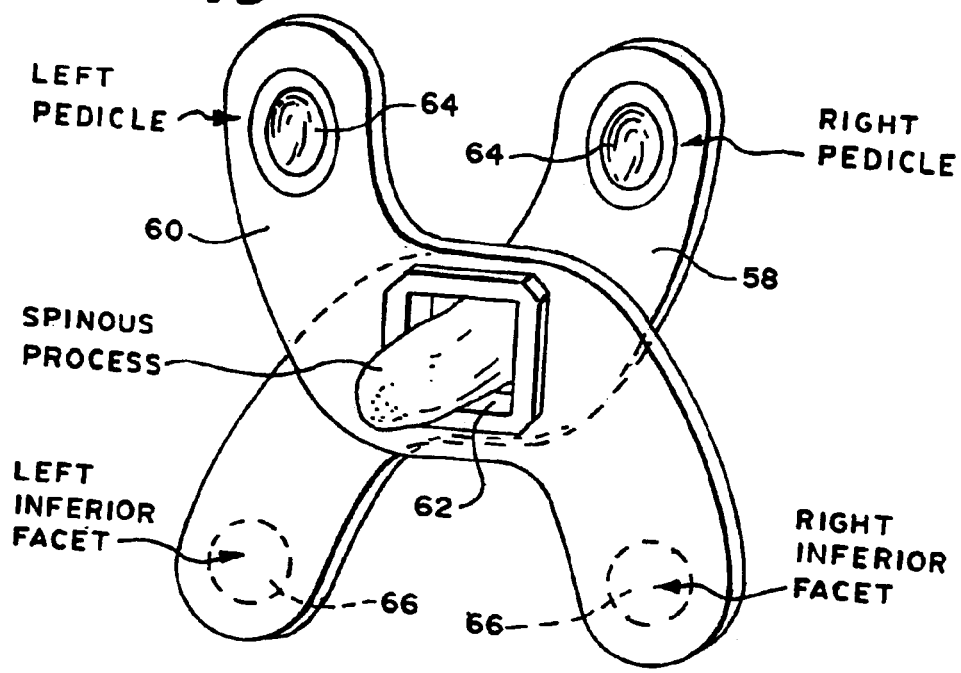
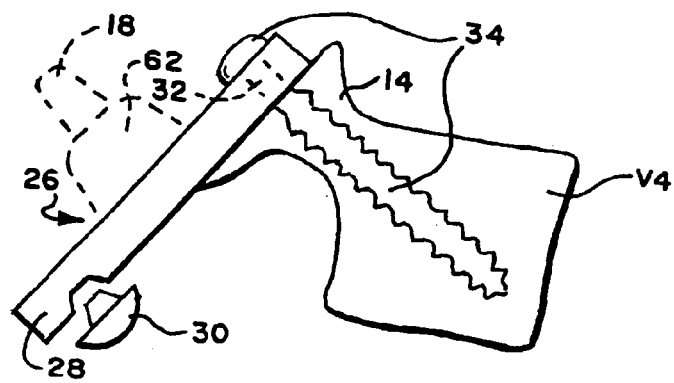
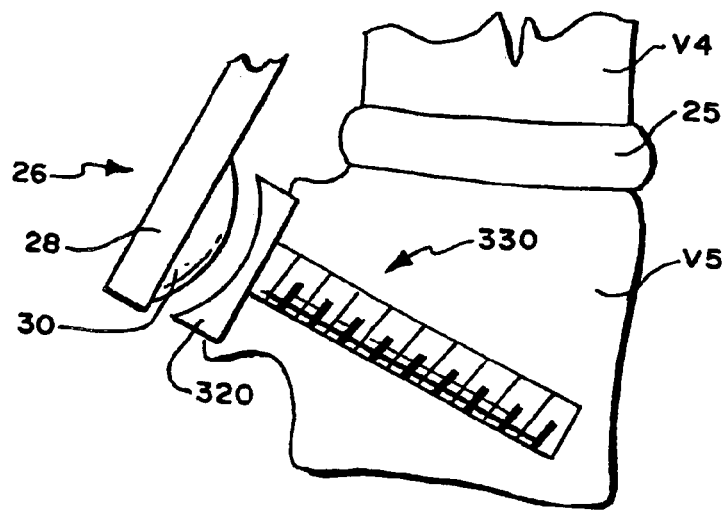

FACET ARTHROPLASTY DEVICES AND METHODS

RELATED APPLICATIONS

This application is a divisional of U.S. patent application Ser. No. 10/615,727, filed Jul. 9, 2003, which is a divisional of U.S. patent application Ser. No. 09/693,272 filed Oct. 20, 2000 (now U.S. Pat. No. 6,610,091), which claims the benefit of U.S. Provisional Patent Application Ser. No. 60/160,891, filed Oct. 22, 1999, which are incorporated herein by reference.

FIELD OF THE INVENTION

The present invention generally relates to devices and surgical methods for the treatment of various types of spinal pathologies. More specifically, the present invention is directed to several different types of spinal joint replacement prostheses, surgical procedures for performing spinal joint replacements, and surgical instruments which may be used to perform the surgical procedures.

BACKGROUND OF THE INVENTION

Back pain is a common human ailment. In fact, approximately 50% of persons who are over 60 years old suffer from lower back pain. Although many incidences of back pain are due to sprains or muscle strains which tend to be self-limited, some back pain is the result of more chronic fibromuscular, osteoarthritic, or ankylosing spondolytic processes of the lumbosacral area. Particularly in the population of over 50 year olds, and most commonly in women, degenerative spine diseases such as degenerative spondylolisthesis and spinal stenosis occurs in a high percentage of the population. Iida, et al, 1989.

Degenerative changes of the adult spine have traditionally been determined to be the result of the interrelationship of the three joint complex; the disk and the two facet joints. Degenerative changes in the disc lead to arthritic changes in the facet joint and vice versa. See Farfan and Sullivan, 1967; see also Farfan, 1969; see also Farfan, 1980.

One cadaver study of 19 cadavers with degenerative spondylolisthesis showed that facet degeneration was more advanced than disc degeneration in all but two cases. Farfan. In mild spondylolisthetic cases, the slip appeared to be primarily the result of predominantly unilateral facet sub-luxation. Other studies into degenerative changes of the spine have revealed extensive contribution of facet joint degeneration to degenerative spinal pathologies such as degenerative spondylolisthesis, central and lateral stenosis, degenerative scoliosis, and kypho-scoliosis, at all levels of the lumbar spine. See Kirkaldy-Willis et al, 1978; see also Rosenberg, 1975.

It has been determined that facet joint degeneration particularly contributes to degenerative spinal pathologies in levels of the lumbar spine with sagittally oriented facet joints, i.e. the L4–L5 level.

When intractable pain or other neurologic involvement results from adult degenerative spine diseases, such as the ones described above, surgical procedures may become necessary. Traditionally, the surgical management of disease such as spinal stenosis consisted of decompressive laminectomy alone. Herkowitz, et al, The Diagnosis and Management of Degenerative Lumber Spondylolisthesis, 1998. Wide decompressive laminectomies remove the entire lamina, and the marginal osteophytes around the facet joint. Because a lot of degenerative spine disease has been demonstrated to be caused by facet joint degeneration or disease, this procedure removes unnecessary bone from the lamina and insufficient bone from the facet joint.

Furthermore, although patients with one or two levels of spinal stenosis tend to do reasonably well with just a one to two level wide decompressive laminectomy, patients whose spinal stenosis is associated with degenerative spondylolisthesis have not seen good results. Lombardi, 1985. Some studies reported a 65% increase in degree of spondylolisthesis in patients treated with wide decompressive laminectomy. See Johnson et al; see also White and Wiltse. The increase in spinal slippage especially increased in patients treated with three or more levels of decompression, particularly in patients with radical laminectomies where all of the facet joints were removed.

To reduce the occurrence of increased spondylolisthesis resulting from decompressive laminectomy, surgeons have been combining laminectomies, particularly in patients with three or more levels of decompression, with multi-level arthrodesis. Although patients who undergo concomitant arthrodesis do demonstrate a significantly better outcome with less chance of further vertebral slippage after laminectomy, arthrodesis poses problems of its own. Aside from the occurrence of further spondylolisthesis in some patients, additional effects include non-unions, slow rate of fusion even with autografts, and significant morbidity at the graft donor site. Furthermore, even if the fusion is successful, joint motion is totally eliminated at the fusion site, creating additional stress on healthy segments of the spine which can lead to disc degeneration, herniation, instability spondylolysis, and facet joint arthritis in the healthy segments.

An alternative to spinal fusion has been the use of an invertebral disc prosthesis. There are at least 56 artificial disc designs which have been patented or identified as being investigated. McMillin C. R. and Steffee A. D., 20th Annual Meeting of the Society for Biomaterials (abstract)(1994). Although different designs achieve different levels of success with patients, disc replacement mainly helps patients with injured or diseased discs; disc replacement does not address spine pathologies such as spondylolisthesis and spinal stenosis caused by facet joint degeneration or disease.

SUMMARY OF THE INVENTION

There is a need in the field for prostheses and prosthetic systems to replace injured and/or diseased facet joints, which cause, or are a result of, various spinal diseases. There is also a need for surgical methods to install such prostheses. There is also a need for prostheses and prosthetic systems to replace spinal fusion procedures.

The present invention overcomes the problems and disadvantages associated with current strategies and designs in various treatments for adult spine diseases. The present inventive spinal arthroplastic systems avoid the problems of spine stiffness, increased loads on unfused levels, and predictable failure rates associated with spinal arthrodesis.

The present invention pertains to spinal prostheses designed to replace facet joints and/or part of the lamina at virtually all spinal levels including L1–L2, L2–L3, L3–L4, L4–L5, L5-S-1, T11–T12, and T12–L1. Various types of joint replacement prostheses are described for treating different types of spinal problems.

One aspect of the invention provides a prosthesis assembly to replace all or a portion of a caudal portion of a left natural facet joint (i.e., a left superior articular process) and all or a portion of a caudal portion of a right natural facet joint (i.e., a right superior articular process) on a vertebral body. The prosthesis assembly comprises a left prosthesis body accommodating fixation to the vertebral body at or near a left pedicle and without support by a lamina. An artificial left facet joint structure is carried by the left prosthesis body and is adapted and configured to replace all or a portion of a caudal portion of the left natural facet joint. The prosthesis assembly also comprises a right prosthesis body accommodating fixation to the vertebral body at or near a right pedicle and without support by a lamina. An artificial right facet joint structure is carried by the right prosthesis body and is adapted and configured to replace all or a portion of a caudal portion of the left natural facet joint.

Another aspect of the invention provides a method of replacing, on a vertebral body, all or a portion of a caudal portion of left natural facet joint (i.e., a left superior articular process) and all or a portion of a caudal portion of a right natural facet joint (i.e., a right superior articular process) using the prosthesis assembly described in the preceding paragraph, to provide improved support for the spinal column. The method comprises the steps of removing all or a portion of the caudal portions of the left and right natural facet joints from the vertebral body, and fixing the prosthesis assembly to the vertebral body to replace both removed caudal portions of the left and right natural facet joints with the artificial facet joint structure.

In one embodiment, at least one of the artificial left and right facet joint structures is adapted and configured to articulate with a cephalad portion of the respective one of the left and right facet joints (i.e., an inferior articular process) of an adjoining vertebral body.

Features and advantages of the inventions are set forth in the following Description and Drawings, as well as in the appended claims.

BRIEF DESCRIPTION OF THE DRAWINGS

FIG. 28 is a superior view of the L4 and L5 vertebrae in a separated condition;

FIG. 29 is a front elevation view of a single-side prosthesis that embodies the feature of the invention;

FIG. 30 is a side elevation view of the prosthesis shown in FIG. 29;

FIG. 31 is a lateral view of the L3, L4, and L5 vertebrae, with the prosthesis shown in FIG. 29 secured to the L4 vertebral body;

FIG. 40 is a front elevation view of the double-side facet joint link assembly shown in FIG. 36 in relation to its location on a vertebral body;

FIG. 41 is a side view of a prosthesis, like that shown in FIGS. 29, 34, or 36, secured for use on the pedicle of a vertebral body (shown in lateral view); and FIG. 42 is a side view of the lower end of the prosthesis shown in FIG. 41, forming the inferior half of a facet joint, the superior half of the facet joint being formed by a superior universal facet prosthesis shown in FIG. 2.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

I. Anatomy of Lumbar Vertebrae

Figure 27:
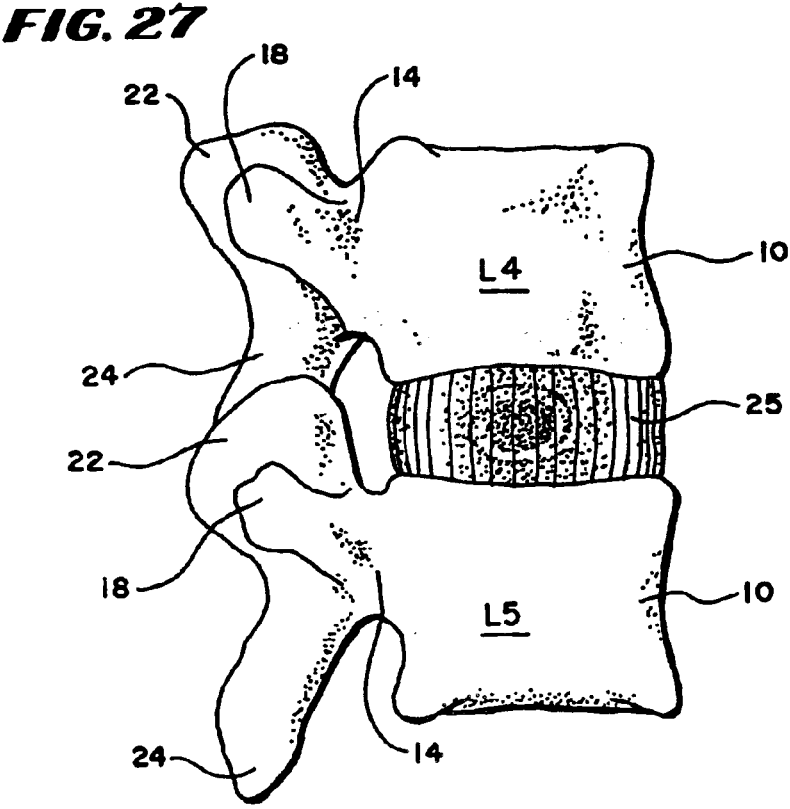
FIG. 27 is a lateral view of the L4 and L5 vertebrae.

FIGS. 27 and 28 show the fourth and fifth lumbar vertebrae L4 and L5, respectively, in a lateral view (while in anatomic association) and in a superior view (separately). The lumbar vertebrae (of which there are a total of five) are in the lower back, also called the "small of the back."

As is typical with vertebrae, the vertebrae L4 and L5 are separated by an intervertebral disk 25. The configuration of the vertebrae L4 and L5 differ somewhat, but each (like vertebrae in general) includes a vertebral body 10, which is the anterior, massive part of bone that gives strength to the vertebral column and supports body weight. The vertebral arch 12 is posterior to the vertebral body 10 and is formed by the right and left pedicles 14 and lamina 16. The pedicles 14 are short, stout processes that join the vertebral arch 12 to the vertebral body 10. The pedicles 14 project posteriorly to meet two broad flat plates of bone, called the lamina 16.

Seven other processes arise from the vertebral arch. Three processes—the spinous process 18 and two transverse 20 processes—project from the vertebral arch 12 and afford attachments for back muscles, forming levers that help the muscles move the vertebrae. The remaining four processes, called articular processes, project superiorly from the vertebral arch (and are thus called the superior articular processes 22) and inferiorly from the vertebral arch (and are thus called the inferior articular processes 24). The superior and inferior articular processes 22 and 24 are in opposition with corresponding opposite processes of vertebrae superior and inferior adjacent to them, forming joints, called zygapophysial joints or, in short hand, the facet joints or facets. The facet joints permit gliding movement between the vertebrae L4 and L5. Facet joints are found between adjacent superior and inferior articular processes along the spinal column.

The facet joints can deteriorate or otherwise become injured or diseased, causing lack of support for the spinal column, pain, and/or difficulty in movement.

As described in this Specification, a facet joint has a superior half and an inferior half. The superior half of the joint is formed by the vertebral level below the joint, and the inferior half of the joint is formed by the vertebral level above the joint. For example, in the L4–L5 facet joint, the superior half of the joint is formed by structure on the L-5 vertebra, and the inferior half of the joint is formed by structure on the L-4 vertebra.

II. Superior Universal Facet Prosthesis

A. Structure

Figure 1:
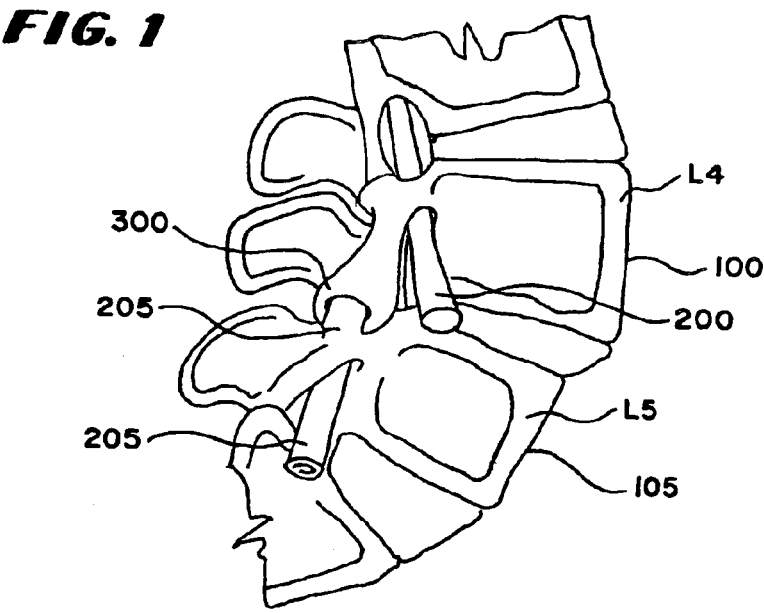
FIG. 1 is a lateral view of a spine with degenerative spondylolisthesis at L4–L5.

A superior universal facet prosthesis 330 is shown in FIG. 1 that embodies features of the invention. The prosthesis 330 is designated "superior" because it creates an artificial facet surface for the superior half of the facet joint. The artificial surface articulates with the inferior half of the facet joint. The prosthesis 330 allows for the replacement of injured, diseased and/or deteriorating components along the superior half of facet joints, to provide improved support for the spinal column.

The universal facet prosthesis 330 may be constructed and configured in various ways. The universal facet prosthesis 330 may, e.g., comprise a cup member 315. The cup member 315 itself may be made of various materials commonly used in the prosthetic arts including, but not limited to, polyethylene, rubber, titanium, titanium alloys, chrome cobalt, surgical steel, or any other total joint replacement metal and/or ceramic, bony in-growth surface, sintered glass, artificial bone, any uncemented metal or ceramic surface, or a combination thereof. The cup member 315 may also be any appropriate shape including, but not limited to, rectangular, disc shaped, trough shaped, or cup shaped. The cup member may be fixed or anchored directly to a vertebra with poly(methylmethacrylate) bone cement, hydroxyapatite, screws, nails, bolts, anchors, break-away anchors and/or wires to facilitate any future removal of the prosthesis, or a combination thereof, or any other means known in the art.

Figure 2:
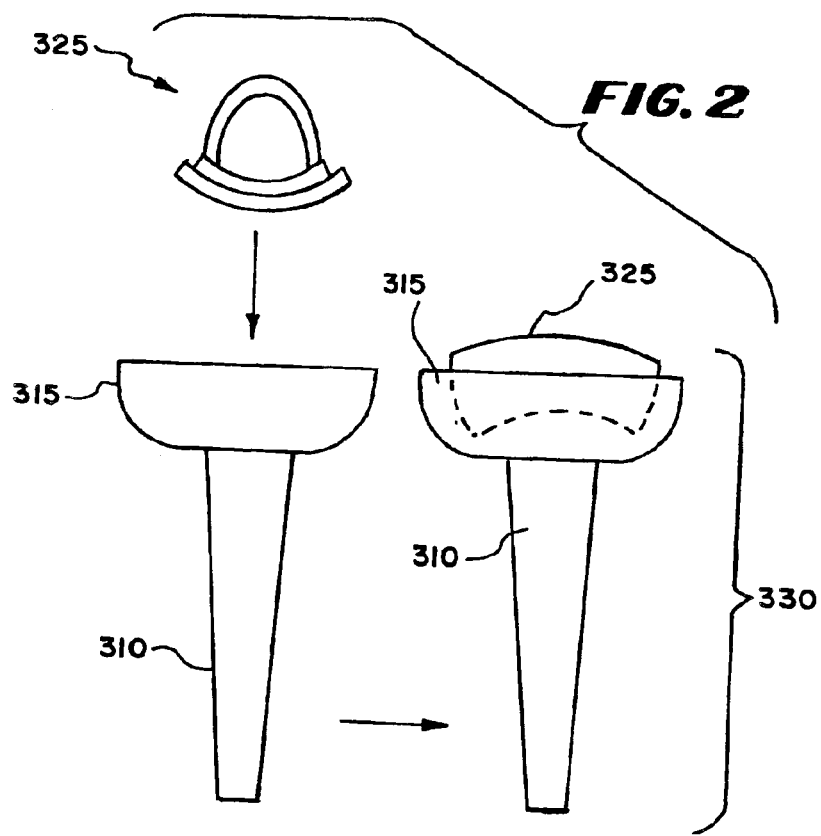
FIG. 2 is a front view of a universal facet replacement prosthesis.

As shown in FIG. 2, the cup member 315 is made of any joint materials commonly used in the prosthetic arts, including, but not limited to, metals, ceramics, titanium, titanium alloys, tantalum, chrome cobalt, surgical steel, bony in-growth surfaces, artificial bone, uncemented surface metals or ceramics, or any combination thereof, preferably covered with a bony in-growth surface.

In the illustrated embodiment, the cup member 315 is fixed to a stem 310, e.g., pre-welded, or glued with a biocompatible adhesive, or removably secured using a frictional Morse taper. If desired, the stem 310 can incorporate one or more fins or ribs (not shown), extending outward from the stem 310, which desirably reduce and/or eliminate rotation of the stem 310 once positioned within the targeted bone. In addition, the stem 310 can be cannulated, if desired, to allow the use of guide pins during insertion of the stem, as is well known in the art.

The stem 310 may itself be made of any joint materials commonly used in the prosthetic arts, including, but not limited to, metals, ceramics, titanium, titanium alloys, tantalum, chrome cobalt, surgical steel, bony in-growth surfaces, artificial bone, uncemented surface metals or ceramics, or a combination thereof. In a preferred embodiment, the stem 310 is covered with a bony in-growth surface.

In the illustrated embodiment, the cup member 315 carries a surface member, which is made of a material, e.g. polyethylene, ceramic, or metal, which provides glide and cushioning ability for any potential contacting components, such as the articular head members described below. In one embodiment (see FIG. 2b), the surface member 325 can be formed in a gently upwardly curving shape, similar in shape to a catcher's mitt. In another embodiment (see FIG. 2c), the surface member 325 is rectangular in shape with rounded corners. The cup member 315 is sized to be larger than the articulating superior half of the facet joint, to allow for motion of the joint.

The surface member 325 may be a separate component that is fixed to the cup member 315, e.g., with a biocompatible adhesive, screws, nails, or comprise a formed part of the cup member 315. The surface member 325 may also be held into the cup member 315 with compressive forces or friction (e.g., using a Morse taper).

Figure 2A:
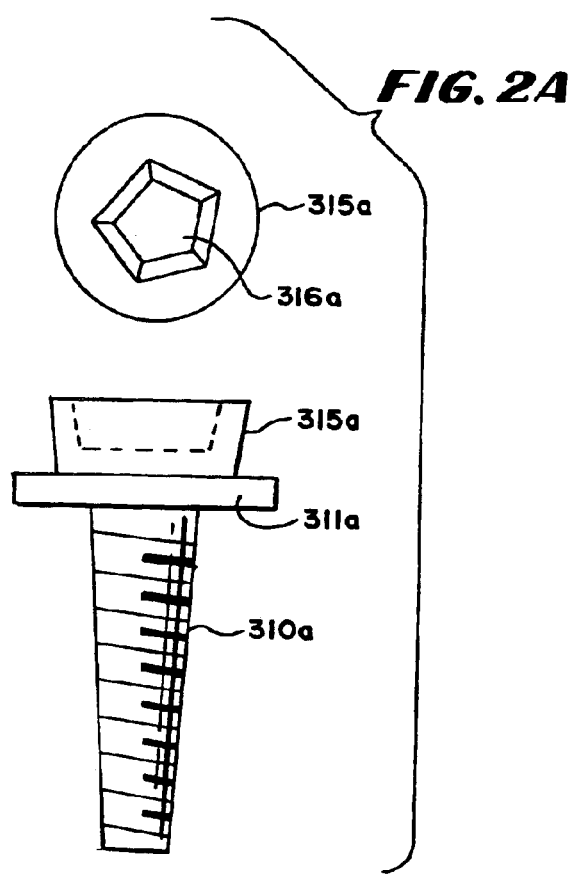
FIGS. 2A, 2B, and 2C are view of an alternative embodiment of a universal facet replacement prosthesis.
Figure 2B:
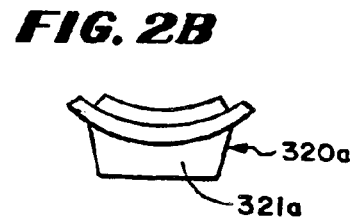
Figure 2C:
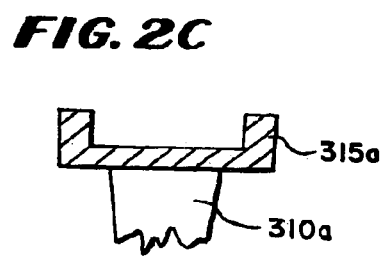

As shown in FIGS. 2a and 2b, the stem 310a could alternately comprise a threaded portion, such as in a pedicle screw, with the head or pedestal 315a incorporating a depression 316a sized to accommodate a hexagonal driver or other surgical driving tool well know in the art. In addition, the prosthesis 320a could incorporate a lower insert 321a sized to fit into the depression 316a in the head 315a. If desired, the insert 321a could comprise a Morse taper. In this embodiment, the stem 310a can be screwed into the bone, with the insert 321a positioned or otherwise secure within the depression 316a. The stem 310a could be placed by tapping without screwing. If revision surgery is required, or some other condition required removal of the prosthesis, the insert 321a can be removed from the stem 310a, and the stem 310a can subsequently be removed from the bone.

As FIG. 2a shows, the stem 310a can also include an enlarged projection or collar 311a abutting the cup member 315a. The collar 311a serves to prevent unintended ingress of the stem 310a further into the pedicle, beyond a desired distance.

Figure 3:
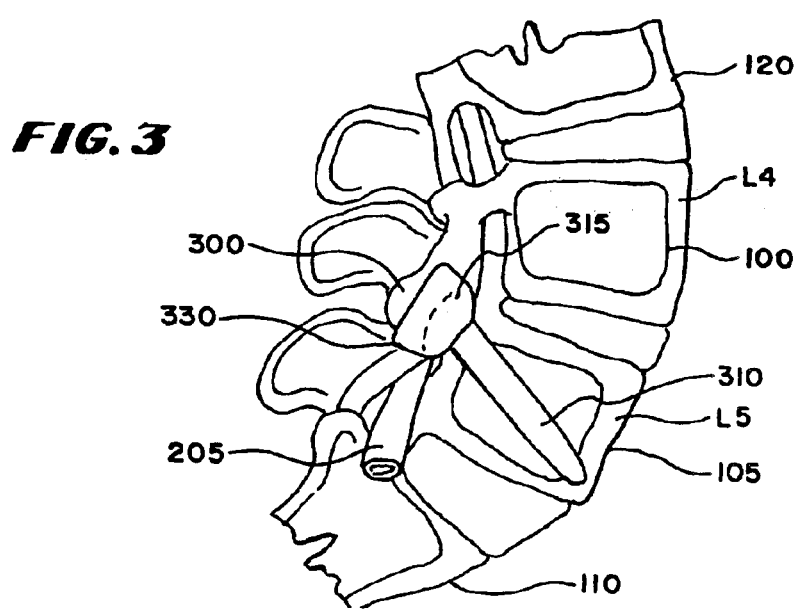
FIG. 3 is a lateral view of a spine with a superior universal facet prosthesis installed in a L5 vertebra.
Figure 4:
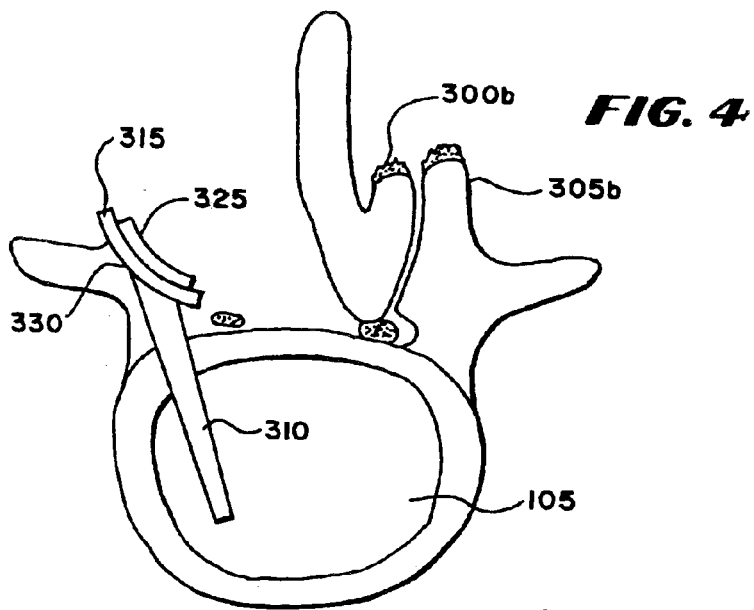
FIG. 4 is a superior view of a L5 vertebra with an installed superior universal facet prosthesis.

FIG. 1 depicts a spondylolisthetic spine with slippage at the L4–L5 joint between the L4 and L5 vertebrae. FIG. 3 and FIG. 4 depict a universal facet prosthesis 330 which has been installed into an L5 vertebra 105 to replace the inferior half 305 of a facet joint. In one embodiment, the stem 310 of universal facet prosthesis 330 is fixed into the L5 vertebra 105 with poly(methylmethacrylate) bone cement, hydroxyapatite, a ground bone composition, or a combination thereof. In another embodiment, both the stem 310 and the cup member 315 are fixed to a vertebra with stainless steel wire to provide addition stability.

The new support provided by a universal facet prosthesis 330 helps correct degenerative spine diseases such as spondylolisthesis, spinal stenosis, or any spine disease. As demonstrated by comparing FIG. 1 showing a spondylolisthetic spine with slippage between the L4 vertebra 100 and the L5 vertebra 105 with FIG. 3 where the diseased superior half 305 of the facet joint has been replaced with a superior universal facet prosthesis 330 of the present invention, correcting spondylolisthesis at the L4–L5 joint and preventing further spondylolisthesis. Similarly, where correction of scoliosis and/or kypho-scoliosis is desired, the size and/or shape of the prosthesis may be chosen to re-orient the affected level(s) of the spine.

The superior universal facet prosthesis 330 described above may be used as a replacement for the superior half of one or more of facet joints at any facet joint at any level of the spine. In the preferred embodiment, the universal facet prosthesis 330 is used to replace the superior half of one or more facet joints in one or more facet joints. The superior facet prosthesis 330 is designed such that it has the appropriate cephalad and caudad directions as well as the appropriate medial/lateral angulation for the given level of the spine where the implant occurs.

In further embodiments, one or more surfaces of a universal facet prosthesis 330 may be covered with various coatings such as antimicrobial, antithrombotic, and osteoinductive agents, or a combination thereof. See, e.g., U.S. Pat. No. 5,866,113, which is incorporated herein by reference. These agents may further be carried in a biodegradable carrier material with which the pores of the stem and/or cup member of certain embodiments may be impregnated. See, e.g., U.S. Pat. No. 5,947,893, which is also incorporated herein by reference.

In still further embodiments of the present invention, a universal facet prosthesis may be attached to strengthened or fortified bone. Vertebrae may be strengthened prior to or during fixation of the prostheses using the methods, e.g., described in U.S. Pat. No. 5,827,289, which is incorporated herein by reference. This type of bone strengthening is particularly suggested for osteoporotic patients who wish to have facet replacement.

Figure 5:
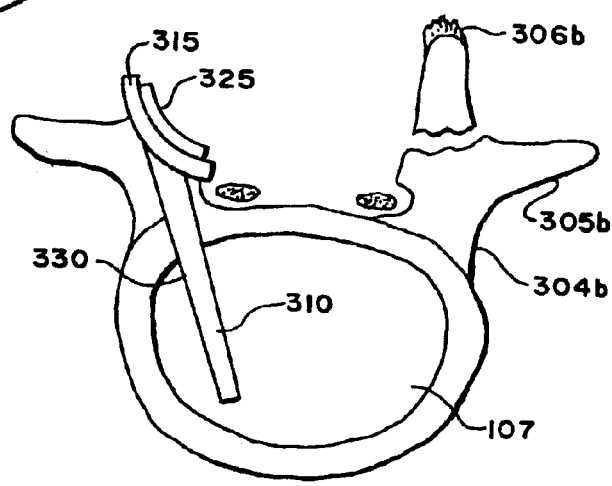
FIG. 5 is a superior view of a L5 vertebra depicting removal of the prominent bone of the superior articular process.
Figure 6:
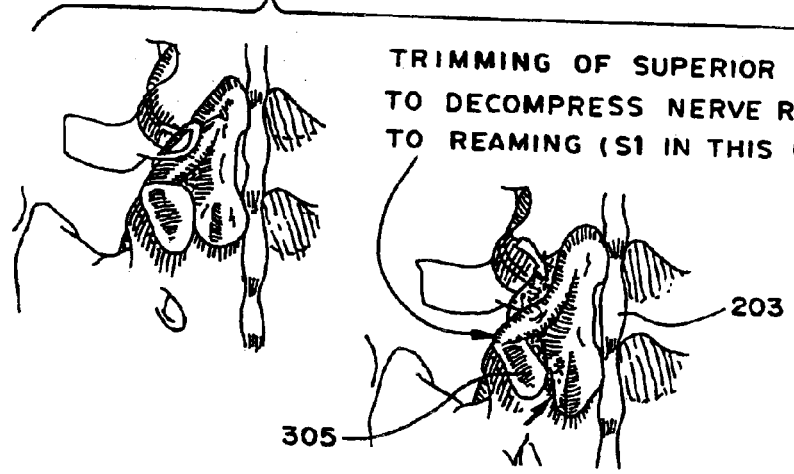
FIG. 6 is a diagram illustrating the trimming of the superior facet to decompress a nerve root prior to reaming.
Figure 7:
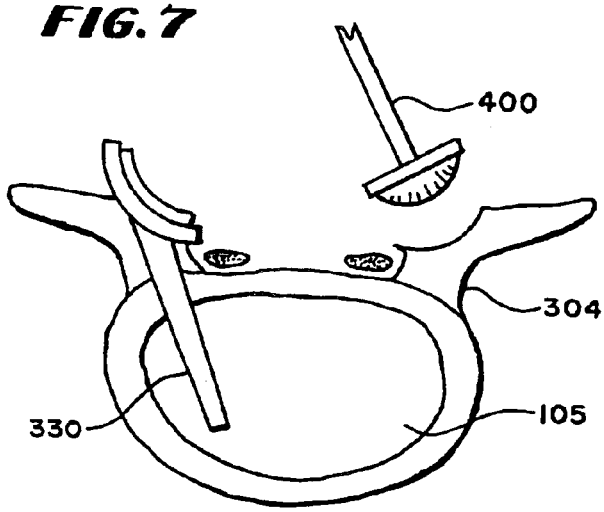
FIG. 7 is a superior view of a L5 vertebra depicting the reaming of the facet into the pedicle.
Figure 8:
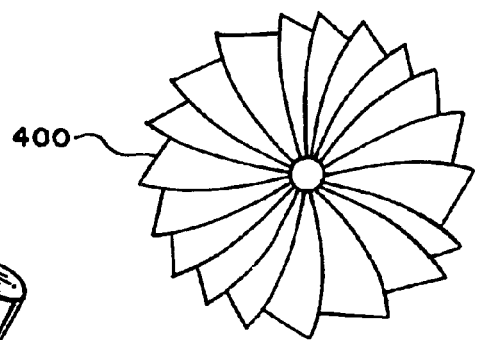
FIG. 8 is a front view of a facet reamer.

B. Surgical Method for Facet Replacement Using the Superior Universal Facet Prosthesis A surgical procedure that embodies features of the invention replaces the superior half of a facet joint with the superior universal facet prosthesis 330 described above. The surgical procedure comprises exposing the spinous process, lamina, and facet joints at a desired level of the spine using any method common to those of skill in the medical arts. The prominent bone 306b (see FIG. 5) may then be rongeured using any means common in the field. The superior facet 305 may also be trimmed, as depicted in FIG. 6, to decompress the nerve root 203. A reamer 400, or any other instrument that is useful for grinding or scraping bone, may be used to ream the facet 305b into the pedicle 304b as depicted in FIG. 7 and FIG. 8.

Figure 9:
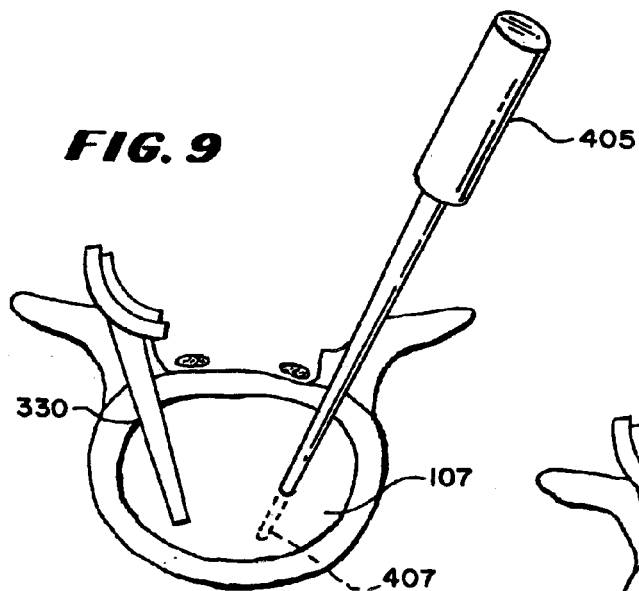
FIG. 9 is a superior view of a vertebral body depicting broaching an opening into a vertebral body.
Figure 10:
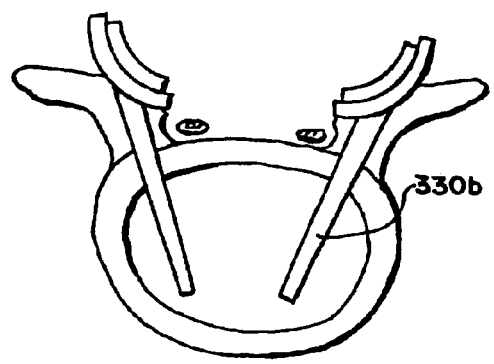
FIG. 10 is a superior view of a vertebral body depicting two universal facet prostheses which have been installed in a vertebral body to form two superior facets.

In a preferred embodiment (see FIG. 9), an opening 407 is made into the vertebral body 107 with a broach 405. The universal facet prosthesis 330b is installed into the opening 407 made by the broach 405, as shown in FIG. 10. The opening 407 may be partly filled with bone cement, hydroxyapatite, or any bone adhesive before installation of the universal facet prosthesis 330b.

In an alternative embodiment, the stem 310 of the superior universal facet prosthesis 330 may be constructed in such a way that the superior universal facet prosthesis 330 can be directly screwed or tapped into the vertebral body 107.

In another arrangement, the cup member 315 of the universal facet member 330 may additionally be fixed to the vertebral body 107 with bone cement, hydroxyapatite, or any other biocompatible adhesive. In yet another arrangement, a universal facet prosthesis without a stem 310 may be attached to the vertebral body with poly (methylmethacrylate) bone cement, hydroxyapatite, screws, nails, bolts, anchors, break-away anchors to facilitate later removal of the prosthesis, or a combination thereof, or any other means known in the art.

In a further embodiment of the present invention, the universal facet prosthesis 330 may be fixed into strengthened or fortified bone. Vertebrae may be strengthened prior to or during fixation of the prosthesis using the methods described in U.S. Pat. No. 5,827,289, which is incorporated herein by reference. This type of bone strengthening procedure is particularly suggested for osteoporotic patients who wish to have facet replacement surgery.

III. Inferior Lamina/Facet Prosthesis

A. Structure

Figure 11:
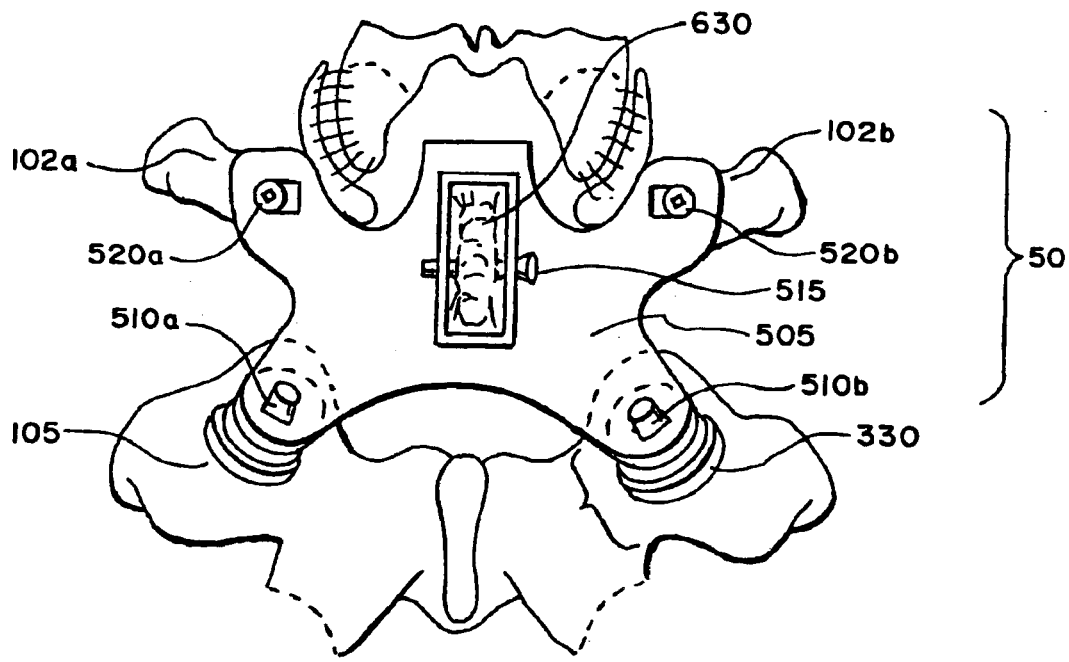
FIG. 11 is a posterior view of a spine depicting an installed inferior lamina/facet prosthesis.

An inferior lamina/facet prosthesis 500 that embodies features of the invention is shown in FIG. 11. The prosthesis 500 is designated "inferior" because it creates an artificial facet surface for the inferior half of a facet joint. The artificial surface articulates with the superior half of the facet joint. The prosthesis 330 allows for the replacement of injured, diseased and/or deteriorating components along the inferior halves of facet joints to provide improved support for the spinal column.

The prosthesis 330 may span the distance from a region on one side of a vertebra to a region of the other side of the vertebra. It can thus replace both inferior halves of a facet joint.

Figure 14:
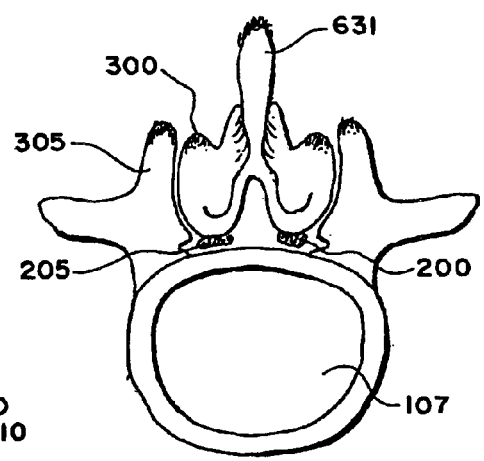
FIG. 14 is a superior view of a vertebral body depicting sagittally oriented arthritic facets with lateral stenosis.

FIG. 14 depicts a superior view of a vertebral body depicting sagitally oriented arthritic facets with lateral stenosis, showing how the spinal process 631 presses forward onto the nerve roots 205 and 200. The prosthesis 500 allows for replacement of diseased and deteriorating inferior regions of the vertebra and partial replacement of lamina (see FIG. 12), which may be pressing on the spinal nerves, to relieve pain. The prosthesis 500 creates artificial facet surfaces for the inferior half of facet joints in the spine, which provide improved support for the spinal column.

Figure 12:
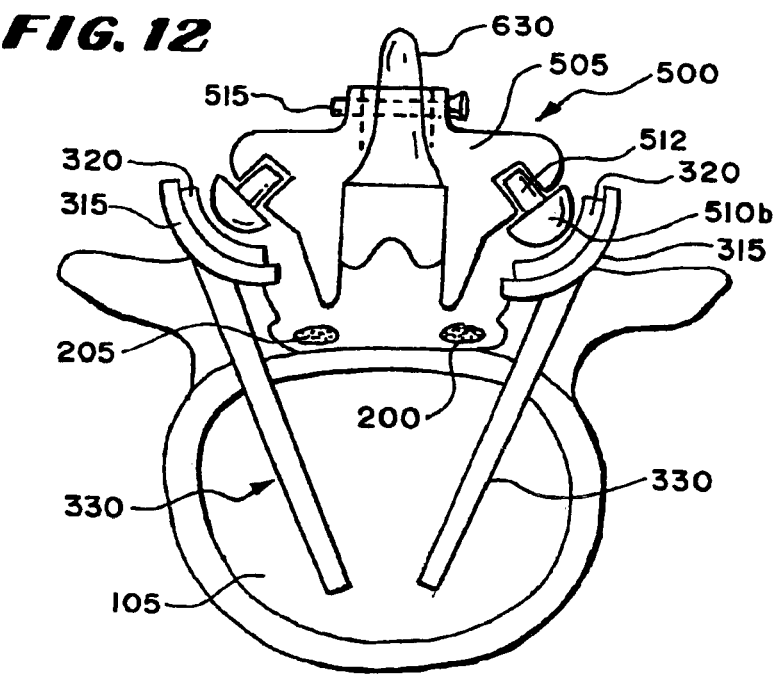
FIG. 12 is a superior view of a vertebral body depicting complete prosthetic facet joints comprising an inferior lamina/facet prosthesis and two superior universal facet prostheses.

As FIG. 12 shows, a superior universal facet prosthesis 330, as described above, may also be installed to replace the superior halves of the facet joints and, with the inferior lamina/facet prosthesis 500 replacing the inferior halves of the facet joints, forming a total facet replacement system that can result in entire artificial facet joints along a length of the spinal column. Alternatively, just the inferior half one or more facet joints, or just the superior half of one or more facet joints, may be replaced. The inferior and/or superior halves of facet joints may be replaced on one side of a given vertebra (unilateral), on the both sides of a given vertebra (bilateral), or a combination of each along a length of the spinal column.

The inferior lamina/facet prosthesis 500 may be constructed in various ways. As shown in FIG. 11, the prosthesis 500 can comprise a base member 505. The base member 505 may be made of any joint materials commonly used in the prosthetic arts, including, but not limited to, metals, ceramics, titanium, titanium alloys, tantalum, chrome cobalt, surgical steel, bony in-growth surfaces, artificial bone, uncemented surface metals or ceramics, or a combination thereof. The base member 505 may also be any appropriate shape to give appropriate support to the spine and to appropriately and sturdily attach to the inferior portions of a vertebral body. The base member 505 may be fixed or anchored directly to the inferior portion of a vertebral body with poly(methylmethacrylate) bone cement, hydroxyapatite, screws, nails, bolts, anchors, break-away screws to facilitate any future removal of the prosthesis, or a combination thereof, or any other means known in the art.

Figure 13:
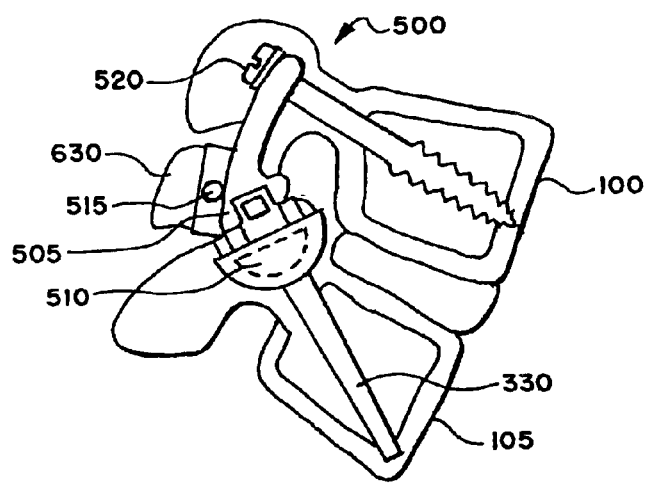
FIG. 13 is a lateral view of an installed complete prosthetic facet joint.

In a preferred arrangement, as depicted in FIG. 11, FIG. 12, and FIG. 13, the base member 505 of the inferior lamina/facet prosthesis 500 is attached to each pedicle 102a and 102b with bilateral pedicle screws 520a and 520b. The base member 505 of the inferior lamina/facet prosthesis 500 may further be attached to the spinous process 630 with a trans-spinous-process screw 515 to provide additional stability.

In another embodiment, the inferior lamina/facet prosthesis 500 may have a head member 510 for articulation with the cup member 315 of a superior universal facet prosthesis 330 or with a superior articular process of the adjoining vertebral body. The head member 510 may be made of various materials commonly used in the prosthetic arts including, but not limited to, polyethylene, rubber, tantalum, titanium, chrome cobalt, surgical steel, bony in-growth surfaces, ceramics, artificial bone, or a combination thereof. The head member 510 may further be any shape which facilitates attachment to the rest of the inferior lamina/facet prosthesis 500 and to smooth connection to, and movement in orientation to, a universal facet prosthesis 330 or a superior articular process of an adjoining vertebral body. In one embodiment, a head member 510 is attached to the base member 505 of the inferior facet/lamina prosthesis 500 with poly(methylmethacrylate) bone cement, hydroxyapatite, screws, nails, bolts, anchors, or any other means known in the art. The head member 510 may also be removably attached by frictional engagement (e.g., using a Morse taper).

In a preferred embodiment (see FIGS. 11 and 12), the inferior facet/lamina prosthesis 500 comprises two head members 510a and 510b formed in the shape of an articular head. The head members 510a and 510b preferably each have a Morse taper 512 at their upper surface to allow them to lock into the base member 505 of the inferior facet/lamina prosthesis 500. Of course, either or both head members 510a and 510b could be formed integrally with the prosthesis 500. In the preferred arrangement, a complete prosthetic facet joint 560 is provided (see FIG. 11), in which the head members 510a and 510b articulate with the cup member 315 of the superior universal facet prosthesis 330.

In further embodiments, one or more surfaces of the inferior lamina/facet prosthesis 500 may be covered with various coatings such as antimicrobial, antithrombotic, and osteoinductive agents, or a combination thereof. See, e.g., U.S. Pat. No. 5,866,113, which is incorporated herein by reference. These agents may further be carried in a biodegradable carrier material with which the pores of the base member and/or any screws, bolts, or nails of certain embodiments may be impregnated. See, e.g., U.S. Pat. No. 5,947,893, which is incorporated herein by reference.

In other arrangements, an inferior lamina/facet prosthesis 500 may be attached to strengthened or fortified bone. Vertebrae may be strengthened prior to or during fixation of the prosthesis using the methods described, e.g., in U.S. Pat. No. 5,827,289, which is incorporated herein by reference. This type of bone strengthening is particularly suggested for osteoporotic patients who wish to have facet replacement.

Figure 15:
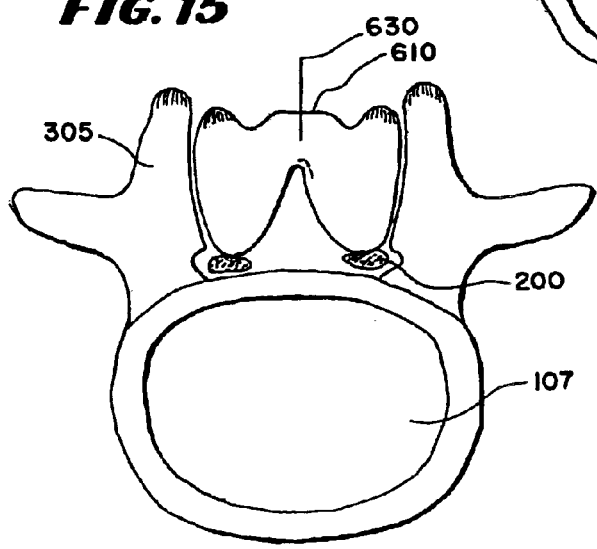
FIG. 15 is a superior view of a vertebral body depicting removal of the inferior one eighth of the spinous process.

B. Surgical Method for Partial Inferior Lamina/Facet Replacement Using the Inferior Lamina/Facet Prosthesis A surgical procedure that embodies features of the invention replaces inferior lamina and articulated processes with the inferior lamina/facet prosthesis 500 as described above. The surgical procedure exposes the spinous process, lamina, and facet joints at a desired level of the spine using any method common to those of skill in the medical arts. As FIG. 15 shows, an inferior one eighth to one half of the spinous process 302 may be cut along the spinous process resection line 610 and removed, if the spinous process appears diseased or damaged. The cutting and removal of the spinous process may be performed using any means common in the field.

Figure 16:
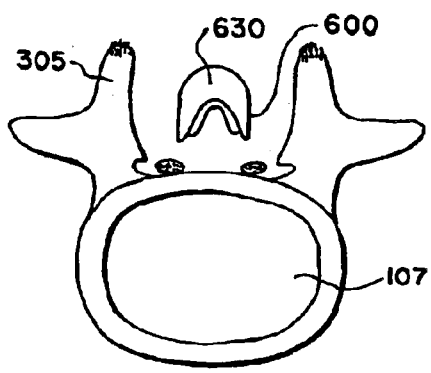
FIG. 16 is a superior view of a vertebral body after an inferior lamina/facet resection.
Figure 17:
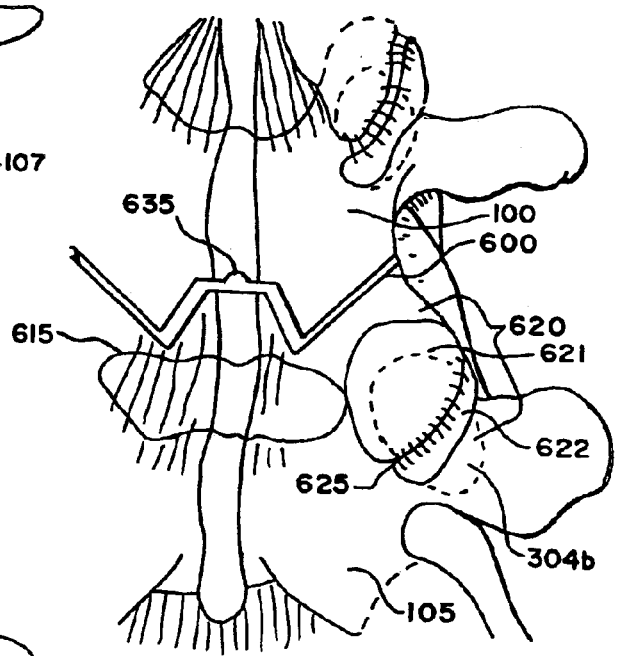
FIG. 17 is a posterior view of a spine at an L4–L5 showing a spinous process resection line and inferior facet resection line.

As shown in FIGS. 16 and 17, the inferior half of the facet joint may also be cut at or near the inferior facet resection line 600. In a preferred embodiment (see FIGS. 16 and 17), most of the lamina 615 is preserved, as is the facet joint capsule 625, which may be opened and folded back. In a preferred embodiment, the facet joint capsule 625 may be cut perpendicular to its direction. The inferior half 621 of the facet joint 620 may then be retracted from the superior half 622. Once the facet joint 620 is separated, the cut inferior bone 615 of the upper joint (i.e. the cut inferior portion of the L4 vertebra in the L4–L5 joint) may be removed. Alternatively, it may be possible to remove the cut inferior bone 615 while simultaneously separating the facet joint 620.

In a preferred embodiment (see FIGS. 18 and 19), a superior universal facet prosthesis 330 is then installed as previously described. Alternatively, the superior universal facet prosthesis 330 may be installed before the inferior bone is removed or even cut.

An inferior lamina/facet prosthesis 500 as described above may be placed onto the facet joints and over the spinous process. The inferior lamina/facet prosthesis 500 may be fixed or anchored to the vertebral body with poly (methylmethacrylate) bone cement, hydroxyapatite, screws, nails, bolts, anchors, break-away screws, or a combination thereof to facilitate any future removal of the prosthesis, or any other means known in the art. In the preferred embodiment (see FIG. 11, FIG. 12, and FIG. 13), the inferior lamina/facet prosthesis 500 is attached to each pedicle 102a and 102b of the inferior facets with bilateral pedicle screws 520a and 520b and is further attached to the spinous process 630 with a trans-spinous-process screw 515 to provide additional stability.

A head member 510 of an inferior lamina/facet prosthesis 500 may articulated into the cup member 315 of the superior universal facet prosthesis 330, or into a inferior half of a facet joint if the inferior half has not been replaced, to create a complete prosthetic facet joint.

Figure 19:
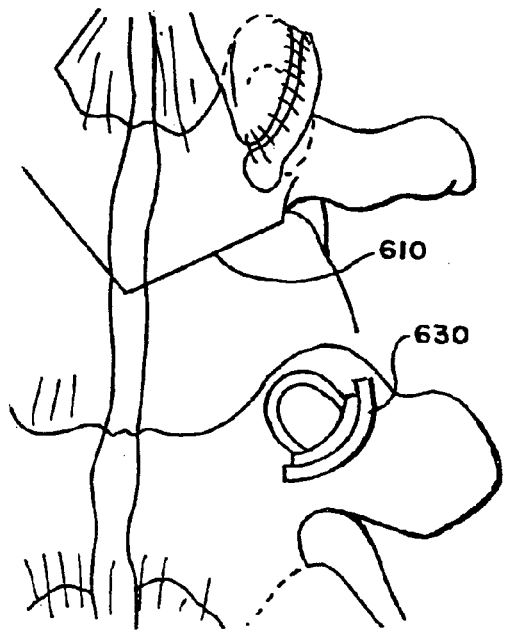
FIG. 19 is a posterior view of an L4–L5 after part of the lamina and inferior facets have been removed with an alternative V-type laminal cut, showing an installed universal facet prosthesis.
Figure 20:
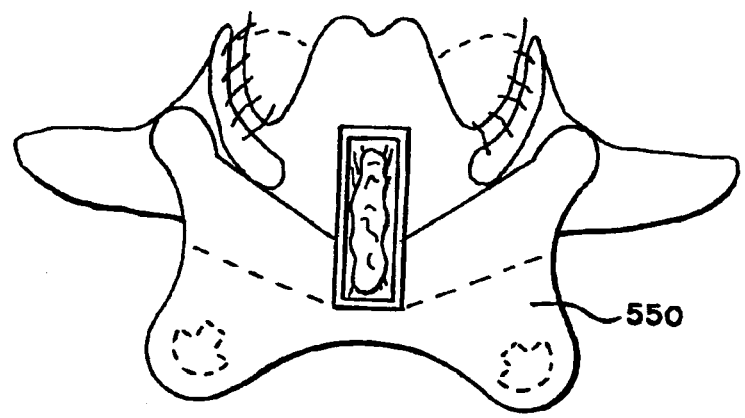
FIG. 20 is a posterior view of a L4 vertebra with an alternative shaped inferior lamina/facet prosthesis installed over a V-type laminal cut.

In an alternative embodiment, as depicted by FIG. 19, the inferior facet resection line 610 may be a V-type cut. If a V-type cut is used, an appropriately shaped inferior lamina/facet prosthesis 550 should be used, such as depicted in FIG. 20. The inferior facet resection line may alternatively be cut in other ways, which are apparent to one of skill in the art of orthopedic surgery and will require inferior lamina/facet prostheses of varying shapes to appropriately fit the cut vertebra.

In a further embodiment of the present invention, a universal facet prosthesis and/or an inferior lamina/facet prosthesis may be fixed into strengthened or fortified bone. Vertebrae may be strengthened prior to or during fixation of the prosthesis using the methods described, e.g., in U.S. Pat. No. 5,827,289, which is incorporated herein by reference. This type of bone strengthening procedure is particularly suggested for osteoporotic patients who wish to have facet replacement surgery.

IV. Hemi-Lamina/Facet Prosthesis

A. Structure

A hemi-lamina/facet prosthesis 700 that embodies features of the invention (see FIG. 21) may be used to replace parts of a lamina and inferior processes, some or all which may have been removed in a primary procedural bone resection, (i.e. with or without wide decompressive laminectomy). The hemi-lamina/facet prosthesis 700 may be designed similarly, or even identically, to the inferior lamina/facet prosthesis 500 described above, depending on how much of the bone is removed.

The hemi-lamina/facet prosthesis 700 may be constructed in various ways. In one embodiment, hemi-lamina/facet prosthesis 700 may, e.g., comprise a base member 705. The base member 705 may be made of any joint materials commonly used in the prosthetic arts, including, but not limited to, metals, ceramics, titanium, titanium alloys, tantalum, chrome cobalt, surgical steel, bony in-growth surfaces, artificial bone, uncemented surface metals or ceramics, or a combination thereof. The base member 705 may be any shape which gives appropriate support to the spine and can be appropriately attached to the bone of the remaining lamina. The base member 705 may be fixed or anchored directly to the inferior portion of a vertebral body with poly(methylmethacrylate) bone cement, hydroxyapatite, screws, nails, bolts, anchors, break-away screws to facilitate any future removal of the prosthesis, a combination thereof, or any other means known in the art.

In a preferred embodiment (see FIG. 21) of a prosthesis for hemiarthroplasty (depicted as cut line 800 and further described below) without decompressive laminectomy, the base member 705 of the hemi-lamina/facet prosthesis 700 is attached to superior pedicle 102b with a pedicle screw 720. In another preferred embodiment, the base member 705 of the hemi-lamina/facet prosthesis 700 may further be attached to the spinous process 630 with a trans-spinous-process screw 715 to provide additional stability.

Figure 22:
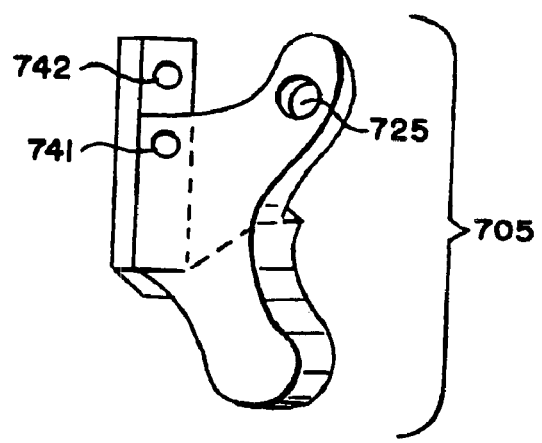
FIG. 22 is a front view of one embodiment of a hemi-lamina/facet prosthesis of the present invention.

In a preferred embodiment (see FIGS. 24 and 25) of a prosthesis for hemiarthroplasty with wide decompressive laminectomy, the hemi-lamina/facet prosthesis 700 comprises at least one base member 705. The base member 705 may further comprise a pedicle attachment hole 725 through which a pedicle screw 720, or a nail, anchor, break-away anchor, bolt, or any other fastening means, may be installed to help secure the hemi-lamina/facet prosthesis 700 to the inferior pedicle. In the preferred embodiment, the base member 705 may also have at least one lamina attachment hole, with two lamina attachment holes 741 and 742 pictured in FIG. 22, to further secure the hemi-lamina/facet prosthesis 700 to the remaining laminal bone with screws, nails, anchors, break-away anchors, bolts, or any other fastening means. Parts of the hemi-lamina/facet prosthesis 700 which overlap bone may be additionally fixed with bone cement, or any biocompatible adhesive.

Figure 24:
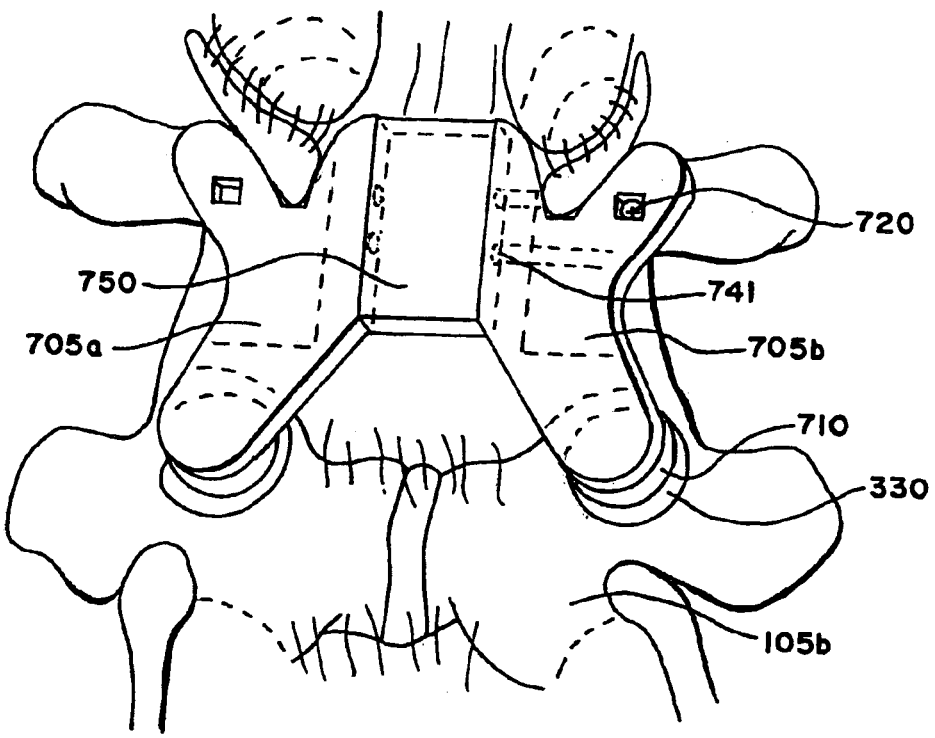
FIG. 24 is a posterior view of one embodiment of an installed hemi-lamina/facet prosthesis of the present invention.

A hemi-lamina/facet prosthesis 700 may further comprise a connection plate, similar to the connection plate 750 depicted in FIG. 24, to connect two base members, i.e. 705a and 705b, together. The connection plate 750 may be fixed to each base member 705a and 705b with a biocompatible adhesive, screws, nails, bolts, compressive force, a combination thereof, or any other means common to those of skill in the art. Alternatively, a hemi-lamina/facet prosthesis 700 may further comprise at least one stabilization bar, similar to the stabilization bars 761 and 762 depicted in FIG. 25. A stabilization bar or bars may be fixed to each base member 705a and 705b with a biocompatible adhesive, screws, nails, bolts, compressive force, a combination thereof, or any other means common to those of skill in the art. A hemi-lamina/facet prosthesis 700 may have any type of bridging or stabilizing members, or no bridging members at all, and may be comprised of any number of base members to provide appropriate stability to the spine. The bridging members may be made of any joint materials commonly used in the prosthetic arts, including, but not limited to, metals, ceramics, titanium, titanium alloys, tantalum, chrome cobalt, surgical steel, bony in-growth surfaces, artificial bone, uncemented surface metals or ceramics, or a combination thereof.

In another embodiment, a hemi-lamina/facet prosthesis 700 may have a head member 710 for articulation with the cup member 315 of a superior universal facet prosthesis 330 or with the superior articular process of an adjoining superior pedicle. The head member 710 may be made of various materials commonly used in the prosthetic arts including, but not limited to, polyethylene, rubber, titanium, chrome cobalt, surgical steel, bony in-growth sintering, sintered glass, artificial bone, or a combination thereof. The head member 710 may further be any shape which allows it to attach to the rest of the hemi-lamina/facet prosthesis 700 and to smoothly connect to, and move in orientation to, the universal facet prosthesis 330 or superior articular facet of the adjoining superior pedicle. In one embodiment, the head member 710 is attached to the rest of the hemi-lamina/facet prosthesis with poly(methylmethacrylate) bone cement, hydroxyapatite, screws, nails, bolts, anchors, a combination thereof, or any other means known in the art. The head member 710 may be removably attached, using, e.g., a Morse taper.

In a preferred embodiment, hemi-lamina/facet prosthesis 700 comprises a head member 710 made in the shape of an articular head. The head member 710 preferably has a Morse Taper at its upper surface to allow it to lock into hemi-lamina/facet prosthesis 700.

In further embodiments, one or more surfaces of a hemi-lamina/facet prosthesis 700 may be covered with various coatings such as antimicrobial, antithrombotic, and osteoinductive agents, or a combination thereof. See, e.g., U.S. Pat. No. 5,866,113, which is incorporated herein by reference. These agents may further be carried in a biodegradable carrier material with which the pores of the base member and/or any screws, bolts, or nails of certain embodiments may be impregnated. See, e.g., U.S. Pat. No. 5,947,893, which is incorporated herein by reference.

In still further embodiments of the present invention, a hemi-lamina/facet prosthesis 700 may be attached to strengthened or fortified bone. Vertebrae may be strengthened prior to or during fixation of the prosthesis using the methods described, e.g., in U.S. Pat. No. 5,827,289, which is incorporated herein by reference. This type of bone strengthening is particularly suggested for osteoporotic patients who wish to have facet replacement.

B. Hemiarthroplasty With or Without Wide Decompressive Laminectomy Using the Hemi-Lamina/Facet Prosthesis A surgical procedure that embodies features of the invention removes at least part of a lamina and at least one superior portion of a facet joint and replacing it with a hemi-lamina/facet prosthesis 700 as described above. The general surgical procedure is generally similar to the inferior lamina/facet replacement previously described, with the main difference being the types of cuts made into the laminal bone, and that two separate prostheses are used to replace the superior portions of two facet joints (left and right) of a given vertebra.

Figure 26:
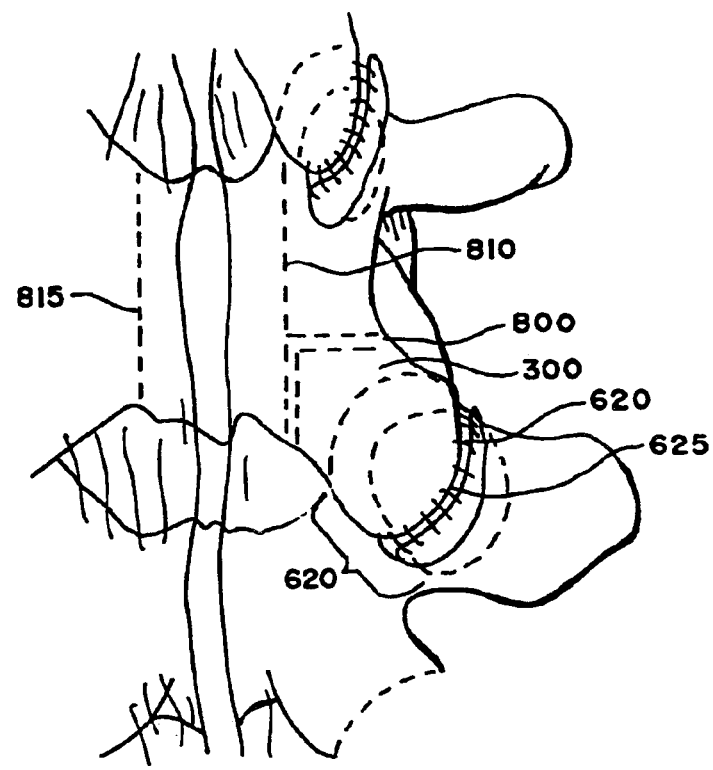
FIG. 26 is a posterior view of the L4–L5 depicting various cuts which may be made into the lamina a facets for a hemiarthroplasty with or without wide decompressive laminectomy.

One embodiment of the surgical procedure comprises exposing the spinous process, lamina, and facet joints at a desired level of the spine using any method common to those of skill in the medical arts. The inferior facet joint and part of the lamina may be cut with a hemiarthroplasty resection line 800 as depicted in FIG. 26 for a hemiarthroplasty. The lamina may additionally be cut for a wide decompressive laminectomy along the decompression resection line 810 as depicted in FIG. 26. The inferior facet joint may be cut on one side or both sides of the lamina. Likewise, the lamina may be cut along a decompression resection line on one side or both sides.

In a preferred embodiment of a hemiarthroplasty without a wide decompressive laminectomy, leaving the cut inferior facet bone 300 in place, the facet joint capsule 625 may be opened and folded back. In the preferred embodiment, the facet joint capsule 625 may be cut perpendicular to its direction. The inferior half 621 of the facet joint 620 may then be retracted from the superior half 622. Once the facet joint 620 is separated, the cut inferior facet bone 825 may be removed. Alternatively, it may be possible to remove the cut inferior facet bone 825 while simultaneously separating the facet joint 620.

Figure 18:
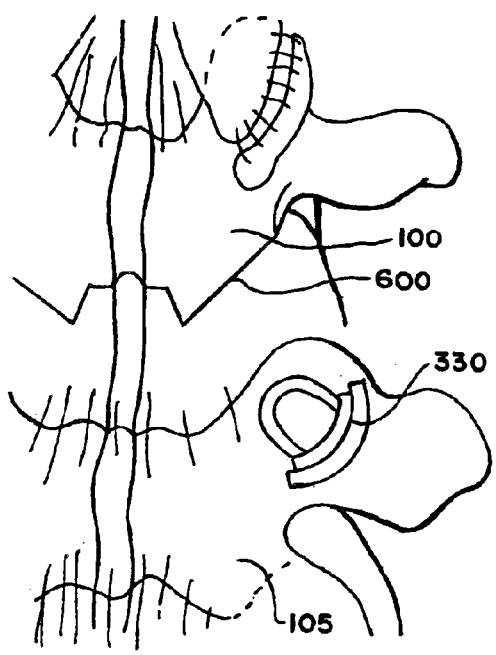
FIG. 18 is a posterior view of an L4–L5 after part of the lamina and inferior facets have been removed, showing an installed universal facet prosthesis.

In a preferred embodiment of a hemiarthroplasty with a wide decompressive laminectomy, a superior universal facet prosthesis 330 is then installed as previously described, and depicted in FIG. 18.

Figure 21:
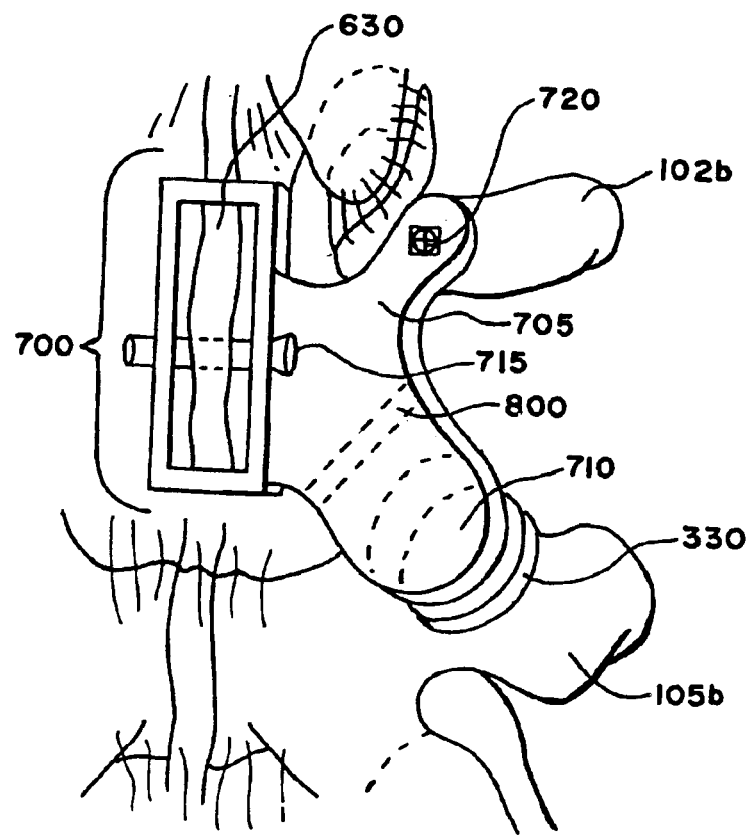
FIG. 21 is a posterior view of one embodiment of an installed hemi-lamina/facet prosthesis of the present invention.
Figure 23:
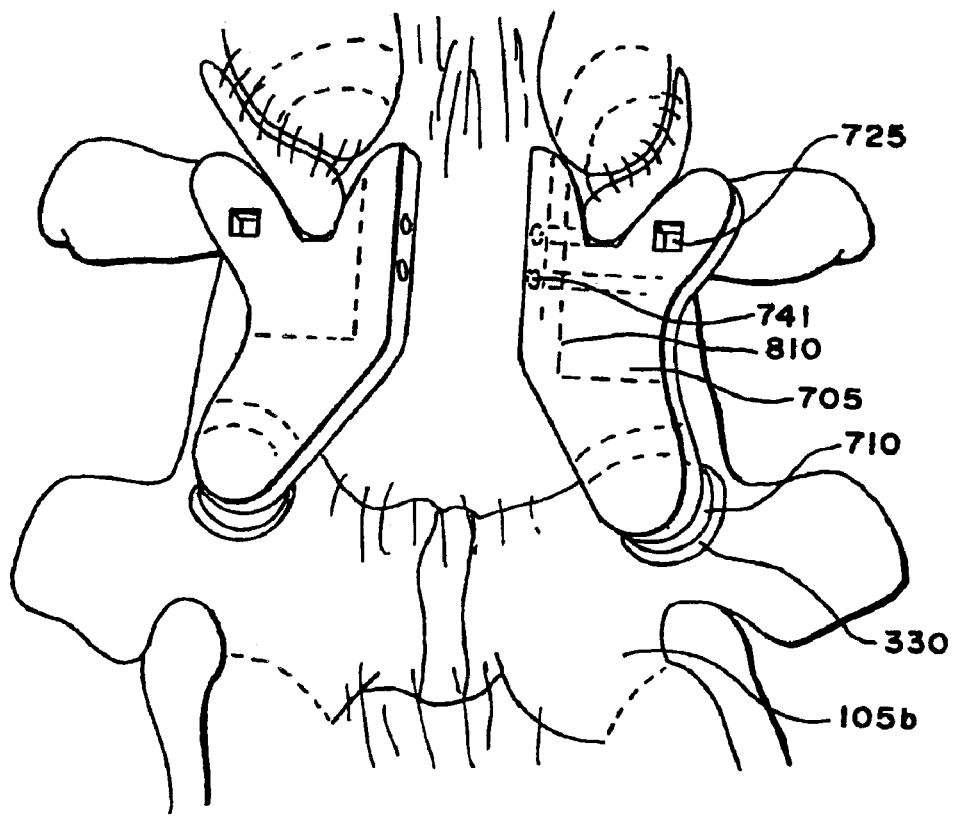
FIG. 23 is a posterior view of a spine, at an L4–L5 joint which has undergone hemiarthroplasty with wide decompressive laminectomy, with two base members of a hemi-lamina/facet prosthesis in the process of being installed onto the L4–L5.

A base member 705 of hemi-lamina/facet prosthesis 700 as described in any of the embodiments above may be placed onto at least one facet joint and at least one pedicle as depicted in FIG. 23, and over the spinous process if it has not been removed for hemiarthroplasty without decompressive laminectomy as depicted in FIG. 21. The hemi-lamina/facet prosthesis 700 may be fixed or anchored to the vertebral body with poly(methylmethacrylate) bone cement, hydroxyapatite, screws, nails, bolts, anchors, break-away screws to facilitate any possible future removal of the prosthesis, a combination thereof, or any other means known in the art. In the preferred embodiment, as depicted in FIG. 21, FIG. 24, and FIG. 25, the hemi-lamina/facet prosthesis 500 is attached to each pedicle with bilateral pedicle screws 720.

A hemi-lamina/facet prosthesis 700 that may be used in hemiathroplasty without wide decompressive laminectomy, depicted in FIG. 21, may further be attached to the spinous process 630 with a trans-spinous-process screw 715 to provide additional stability. A hemi-lamina prosthesis 700 that may be used in hemiathroplasty with wide decompressive laminectomy, as depicted in FIGS. 23, 24, and 25, may further be attached to remaining laminal bone with screws, bolts, nails, anchors, or breakaway anchors through at least one lamina attachment hole 741 to provide additional stability.

Figure 25:
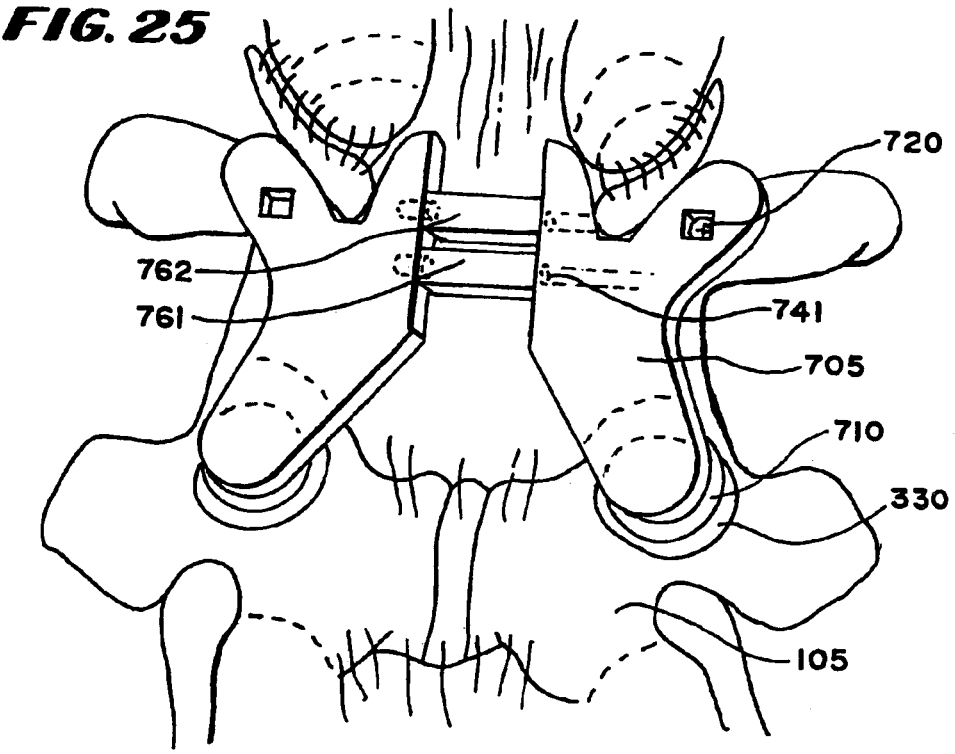
FIG. 25 is a posterior view of one embodiment of an installed hemi-lamina/facet prosthesis of the present invention.

In embodiments where a hemi-lamina/facet prosthesis 700 with more than one base member 705 is installed, a connection plate, depicted as connection plate 750 in FIG. 24, at least one stabilization bar, depicted as stabilization bars 761 and 762 in FIG. 25, or any other connecting or stabilizing means known in the art, may be installed with the base members to provide additional stability to the spine.

At least one head member, depicted as head member 710 in FIGS. 21, 23, 24, and 25, of a hemi-lamina/facet prosthesis 700 may be articulated into a cup member of a superior universal facet prosthesis 330 to create a prosthetic facet joint capsule.

The embodiments may be used to replace one or more facet joints for the entire length of the spine from S1 to T11, on one side of a given vertebra, or both sides of a given vertebra, or a combination thereof along a length of the spine. If only one facet joint at a given level is to be replaced, the unilateral arthroplasty prosthesis for the inferior half of the joint may be fixed to the superior ipso-lateral pedicle and include a box fitted over the spinous process, combined with screw fixation. The spinous process box is similar to the spinous process box in the bilateral total facet arthroplasty embodiment previously discussed.

In a further embodiment of the present invention, a universal facet prosthesis 330 and/or a hemi-lamina/facet prosthesis 700 may be fixed into strengthened or fortified bone. The vertebrae may be strengthened prior to or during fixation of the prosthesis using the methods described, e.g., in U.S. Pat. No. 5,827,289, which is incorporated herein by reference. This type of bone strengthening procedure is particularly suggested for osteoporotic patients who wish to have facet replacement surgery.

V. Other Facet Prostheses

A. Single Side

FIGS. 29 and 30 show an inferior prosthesis 26 that embodies features of the invention. The prosthesis 26 is designated "inferior" because it creates an artificial facet surface in the inferior half of a facet joint. The artificial surface articulates with the superior half of the facet joint. The prosthesis 26 is particularly well suited to single-sided procedures and/or for procedures involving vertebral bodies which are not symmetrical.

When the processes on one side of a vertebral body are differently spaced from those on the other side of the same body, the prostheses on each side would desirably be of differing sizes as well. Moreover, it is often difficult and/or impossible for a surgeon to determine the precise size and/or shape necessary for a prosthesis until the surgical site has actually been prepared for receiving the prosthesis. In such a case, the surgeon typically needs a family of prostheses possessing differing sizes and/or shapes immediately available during the surgery. The surgeon cannot wait for a custom-fitted device to be created during the surgery, so a number of prostheses of varying sizes and/or shapes must be available for each procedure.

The prosthesis 26 can be conveniently formed in different sizes and shapes, to offer an array of prostheses 26 from which the surgeon can pick and choose as surgery proceeds. This allows a surgeon to create a "custom" implant during the surgical procedure.

In the illustrated embodiment (see FIGS. 29 and 30), the prosthesis 26 comprises a body 28 sized and shaped to span the distance between a pedicle 14 and an inferior articular process 24 on the same side of a vertebral body (see FIG. 31). The body 28 may be formed of a material commonly used in the prosthetic arts including, but not limited to, polyethylene, rubber, titanium, chrome cobalt, surgical steel, bony in-growth sintering, sintered glass, artificial bone, or a combination thereof.

The upper section of the body 28 desirably includes an opening 32. The opening 32 accommodates a pedicle screw 34 (see FIG. 41), which secures the upper end of the body 28 into the pedicle 14 of the vertebral body. The opening 32 could be elongated, to allow for varying orientations and/or sizes of the pedicle screw 34. The remainder of the link body 28 can be secured to the exterior of the vertebra using, e.g., biocompatible adhesive.

The lower section of the body 28 is oriented to serve as the superior half of a facet joint. The lower section of the body 28 desirably incorporates a head 30. The head 30 can be permanently affixed to the body 28, using, e.g., adhesive. Alternatively, the head can be frictionally secured, e.g., using a Morse taper, for removal and replacement (as FIG. 41 shows). Like the body 28, the head 30 can be formed of a material commonly used in the prosthetic arts including, but not limited to, polyethylene, rubber, titanium, chrome cobalt, surgical steel, bony in-growth sintering, sintered glass, artificial bone, or a combination thereof. The head 30 possesses a curvilinear shape that desirably curves along a gradual arc (as FIG. 42 shows), or can present a "button" shape.

If desired, the lower section of the joint link body 28 could be angled, to more naturally mimic the orientation of a non-diseased facet joint. In one alternative embodiment, the lower section of the joint link body 28 could rotate relative to the upper section, and could be rotationally secured in a desired position by a surgeon using a locking screw or other locking means known in the art. Such an embodiment would allow the surgeon to alter the orientation of the lower section to fit the particular needs of a patient during the actual surgical procedure.

In use (see FIG. 31), the head 30 articulates with the superior half of the facet joint. The superior facet 22 can comprise the natural superior articular process itself (as FIG. 31 shows), or it can comprise a superior prosthetic facet created, e.g., by the previously described universal facet prosthesis 330 (as FIG. 42 shows). The surface member 320 of the universal facet prosthesis 330 can comprise a metal material made of, e.g., titanium, cobalt, chrome, etc., or a plastic material such as, e.g., polyethylene, or a ceramic material. Thus the surgeon can select the same or different materials to form the joint interface between the head 30 and facet prosthesis 330.

Figure 34:
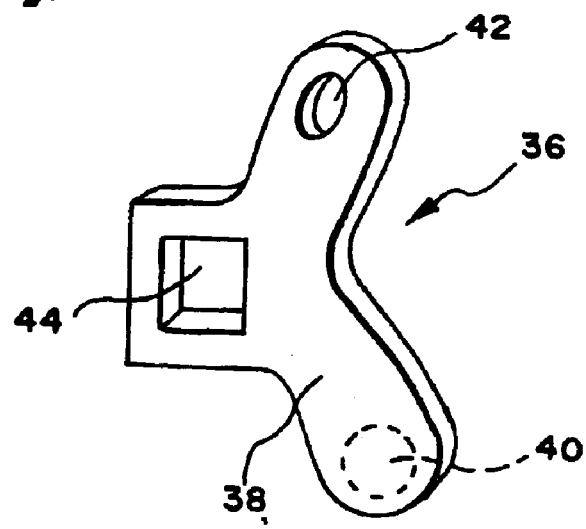
FIG. 34 is a front elevation view of another single-side facet prosthesis that embodies the feature of the invention.
Figure 35:
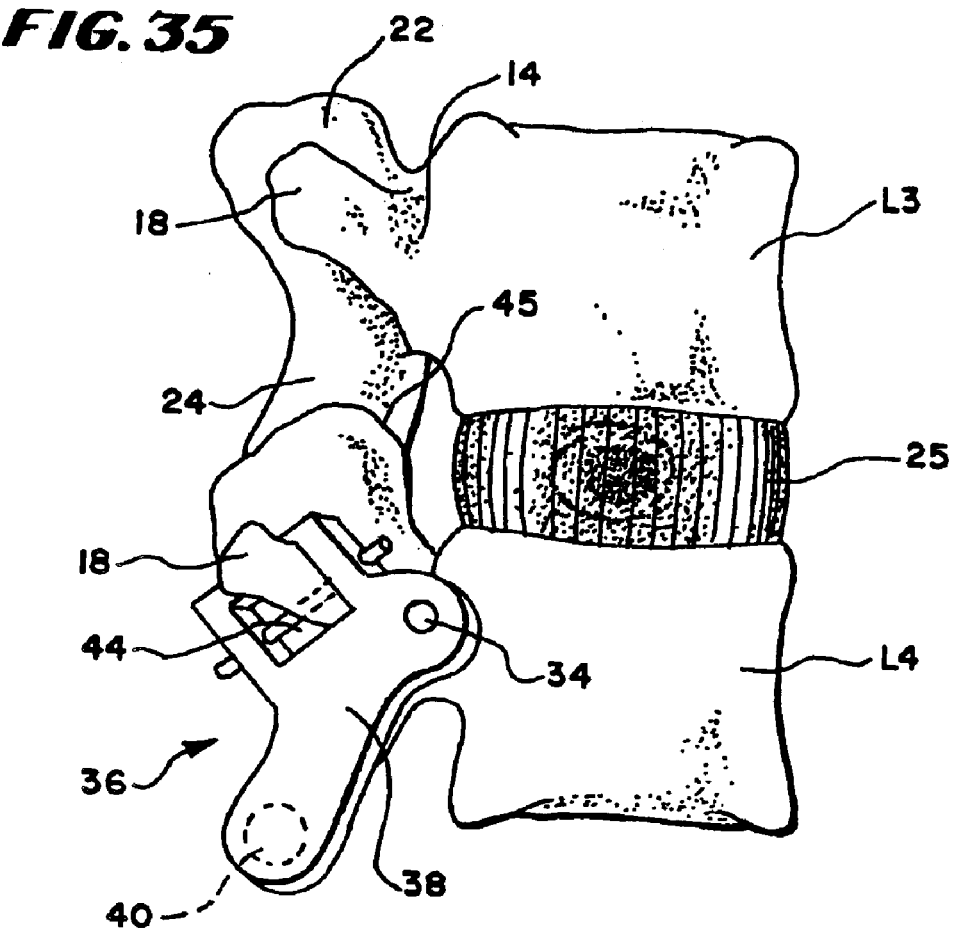
FIG. 35 is a lateral view of the L3 and L4 vertebrae, with the prosthesis shown in FIG. 34 secured to the L4 vertebral body.

FIGS. 34 and 35 show another embodiment of an inferior universal prosthesis 36 that embodies features of the invention. The prosthesis 36, like the prosthesis 26, is designated "inferior" because it creates an artificial facet surface in the inferior half of the facet joint. The artificial surface articulates with the superior half of the facet joint. Like the prosthesis 26, the prosthesis 36 is particularly well suited to single-sided procedures and/or for procedures involving vertebral bodies which are not symmetrical.

The prosthesis 36 comprises a body 38 sized and shaped to span the distance between a pedicle 14 and an inferior articular process 24 (see FIG. 35). The body 38 may be formed of the same types of material as the link body 28. Like the link body 28, the upper section of the joint link body 38 desirably includes an opening 42, to accommodate a pedicle screw 34 (see FIG. 35), which secures the upper end of the body 38 into the pedicle 14 of the vertebral body, in similar fashion as generally shown in FIG. 41. As before described with reference to the link 26, the opening 42 in the link body 38 could be elongated, to allow for varying orientations and/or sizes of the pedicle screw 34. The remainder of the link body 28 can be secured to the exterior of the vertebra using, e.g., biocompatible adhesive.

Unlike the link body 28, the link body 38 includes an intermediate opening 44. In use (see FIG. 35), the spinous process 18 (if present) can extend through the opening 44, to stabilize the link body 38 on the vertebral body. Desirably, a trans-spinous-process screw 45 can be used to provide additional stability.

The lower section of the joint link body 38 is oriented to serve as the inferior half of a facet joint. The lower section of the joint link body 38 desirably incorporates a head 40, which can be constructed in the same fashion as the head 30 of the link 26. Like the head 30, the facet head 40 can be permanently affixed to the body 38 or can be secured in with a frictional fit (e.g., using a Morse taper) for removal and replacement. Like the head 30, the head 40 can be formed of a material commonly used in the prosthetic arts.

In use (see FIG. 35), the head 40 articulates with the superior half of the facet joint with the next adjacent vertebra level. As before explained for the link 26, the superior facet 22 can comprise the natural superior articular facet 22 itself, or it can comprise a prosthetic facet created, e.g., by the previously described universal facet prosthesis 330.

Figure 32:
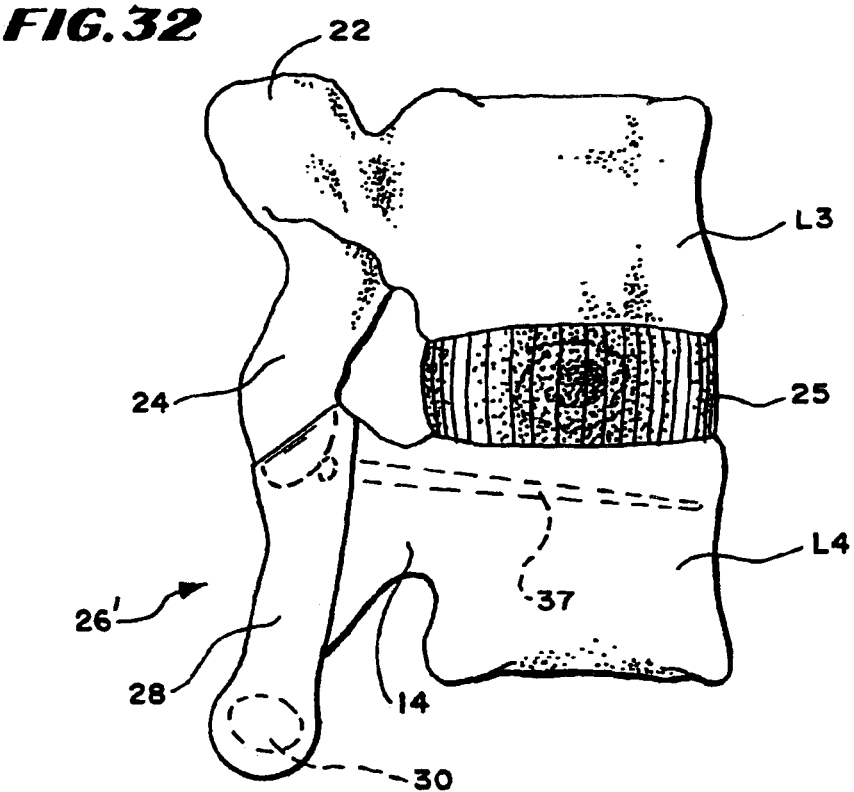
FIG. 32 is a lateral view of the L3 and L4 vertebrae, with a link secured to the L4 vertebral body.

FIG. 32 shows a superior prosthetic link 26' that also embodies features of the invention. The prosthetic link 26' is designated "superior" because it creates an artificial facet surface in the superior half of a facet joint. The artificial surface articulates with the inferior half of the facet joint. The superior prosthesis link 26', like the prosthesis 26, is particularly well suited to single-sided procedures and/or for procedures involving vertebral bodies which are not symmetrical.

A stem 37 extends out from the upper end of the link 26'. The stem 37 is inserted (by screwing or tapping) into the pedicle, to thereby secure the link 26' to the vertebral body.

As FIG. 32 shows, the upper end of the link 26' is shaped to form a cup 36, which articulates with the inferior half of the facet joint.

Figure 33:
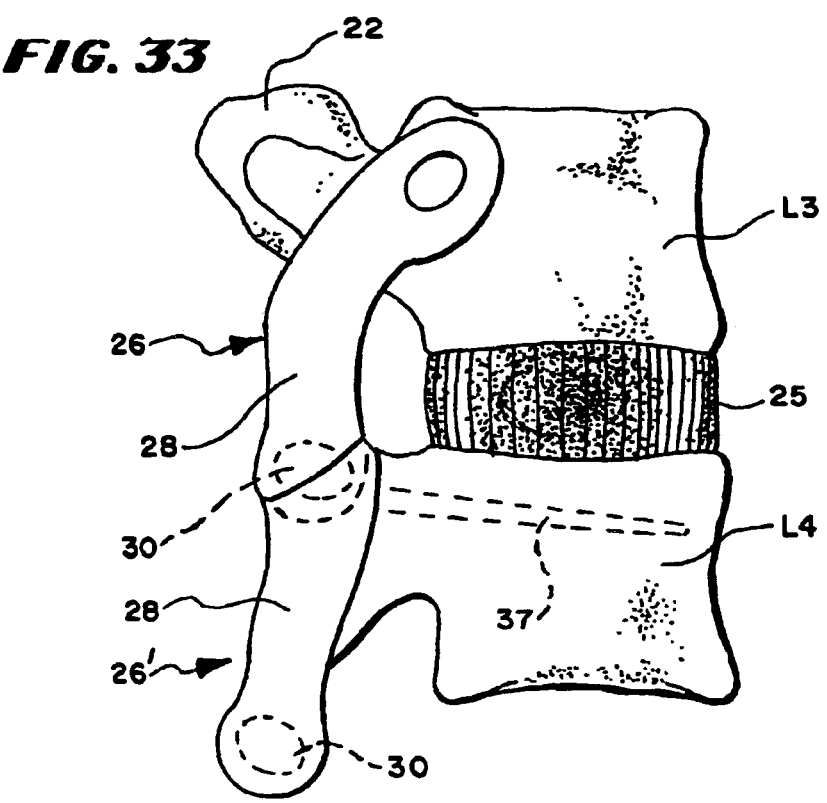
FIG. 33 is a lateral view of the L3 and L4 vertebrae, with a link secured to the L4 vertebral body.

The inferior half of the facet joint can comprise the natural inferior articular process 24 itself (as FIG. 32 shows), or it can comprise the head 30 of an inferior prosthesis 26 or link 26' attached to the next adjacent upper vertebra level (as FIG. 33 shows).

The lower end of the link 26' can also carry a head 30 for articulation with the superior half of a facet joint with the next adjacent lower vertebra. The superior half of the facet joint can comprise the natural superior articular process 22 itself, or it can comprise the cup of a link 26' attached to the next adjacent lower vertebra level.

It can thus be appreciated that the link 26' is well suited for use in procedures requiring replacement of multiple levels of facet joints, and can be interlinked in superior and inferior pairs, like a structure formed out of interlinking tinker-toy pieces. The link 26' also allow subsequent surgeries to build upon already replaced levels, rather than requiring the removal and replacement of an existing implant to accommodate replacement of failing facet joints in an adjacent level. It should be appreciated that the upper end of the prosthesis 36 can also be shaped to form a cup to articulate with the superior half of the facet joint with the next adjacent upper vertebra level.

The prosthesis 26, 36, or link 26' are well suited for use in a single side of the vertebral body, such as where the facet joints need only be replaced on a single side of the vertebral body. The prosthesis 26, 36, or link 26' are also well suited for use in a dual-sided procedure where the vertebral body is either symmetrical or non-symmetrical. In this arrangement, other prostheses 26, 36, or links 26' can be secured on the opposite side of the vertebral body, allowing both sides of the vertebral body to be treated. Because the surgeon can pick prostheses 26, 36, and links 26' of varying sizes, depending upon the size of the vertebral site, and can individually position each prosthesis 26 or link 26' relative to the vertebral body, the surgeon can tailor the linked implant system to the individual's needs.

B. Multiple Level, Sequential Link Assemblies

Figure 36:
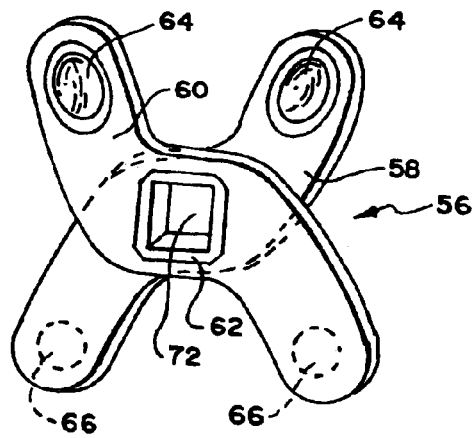
FIG. 36 is a front elevation view of a double-side facet joint link assembly that embodies the feature of the invention, being formed of two criss-crossing, mating link bodies.

FIG. 36 shows a universal prosthetic joint link assembly 56 that embodies features of the invention. The joint link assembly 56 is particularly well suited to double-sided procedures and for sequential, multiple level procedures.

In the illustrated embodiment (see FIG. 36), the joint link assembly 56 comprises two criss-crossing link bodies 58 and 60. Each body 58 and 60 (shown mutually separated in FIGS. 37 and 38, respectively) may be formed of a material commonly used in the prosthetic arts including, but not limited to, polyethylene, rubber, titanium, chrome cobalt, surgical steel, bony in-growth sintering, sintered glass, artificial bone, or a combination thereof.

As FIG. 36 shows, the link bodies 58 and 60 are desirably locked together for use at an intermediate keyway 62, to form the x-shaped, criss-crossing assembly 56. The key-way 62 is formed by a shaped opening 68 in one body 60 (see FIG. 37) and a mating shaped key 70 in the other body 58 (see FIG. 38). The key 70 nests within the opening 60 (as FIG. 36 shows), to frictionally hold the bodies 58 and 60 together and resist relative rotation between the bodies 58 and 60.

Figure 37:
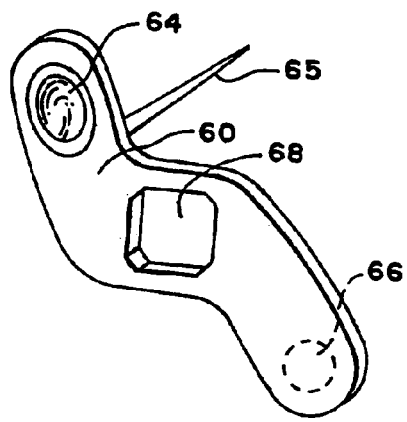
FIGS. 37 and 38 are front elevation views of the link bodies forming the joint link assembly shown in FIG. 36, being shown in a mutually separated condition.
Figure 38:
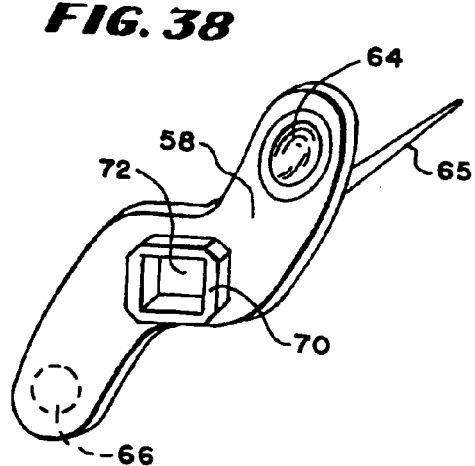
Figure 39:
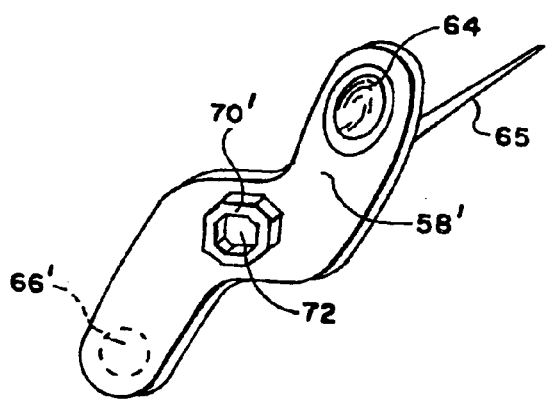
FIG. 39 is a front elevation view of an alternative embodiment of a link body that, when assembled with a mating link body, forms a joint link assembly like that shown in FIG. 36.

Of course, the shape of the opening 68 and key 70 can vary. In FIGS. 36, 37, and 38, the opening 68 and key 70 are generally square or rectilinear in shape. In FIG. 39, an alternative link body 58 is shown, which possesses a key 70' that is generally octagonal in shape, sized to nest within a corresponding octagonal opening in the other link (not shown). In this arrangement, the two link bodies 58 and 60 can be mutually assembled in different arcuately spaced orientations, allowing for variations in facet joint size and positioning. If desired, the key-way 62 could alternately be formed in a tooth and gear arrangement, which would desirably allow a multiplicity of potential arcuately spaced orientations for the two link bodies 58 and 60 forming the assembly 56.

The key 70 desirable peripherally defines an opening 72 (see FIG. 38), through which the spinous process 18 can (if present) project during use. This is generally shown in phantom lines by FIG. 41.

Alternatively, the link bodies 58 and 60 could be formed in a criss-crossing shape as a single, unitary body.

The upper section of each link body 58 and 60 desirably includes a cup 64. The cups 64 form the left and right superior halves of a facet joint and, in use, articulate with the left and right inferior halves of the facet joint.

A stem 65 extends out from the upper end of each link body 58 and 60. The stem 67 is inserted (by screwing or tapping) into the pedicle, to thereby secure the link bodies 58 and 60 to the vertebral body. In use, the stems 67 secure the upper end of the bodies 58 and 60 into an opposite pedicle 14 of a vertebral body.

As FIG. 40 best shows, the bodies 58 and 60 are each sized, shaped and mutually oriented to span the distance between a pedicle 14 on one side of the vertebral body and the region of the inferior articular process on the opposite side of the vertebral body. The remainder of the link bodies 58 and 60 can be secured to the exterior of the vertebra using, e.g., biocompatible adhesive. A trans-spinous-process screw 63 can also be used to provide additional stability.

The lower section of each link body 58 and 60 is oriented to serve as the inferior half of a facet joint. As FIG. 40 shows, the link body 58, secured to the right pedicle, is positioned to serve as the inferior half of the facet joint on the left side of the vertebra. The link body 60, secured to the left pedicle, is positioned to serve as the inferior half of the facet joint on the right side of the vertebra. For this purpose, the lower section of each link body 58 and 60 desirably incorporates a head 66. As before explained, the head 66 can be permanently affixed to each body 58 and 60 or it can be secured in a frictional way using, e.g., a Morse taper for removal and replacement. Like the bodies 58 and 60, the head 66 can be formed of a material commonly used in the prosthetic arts including, but not limited to, polyethylene, rubber, titanium, chrome cobalt, surgical steel, bony in-growth sintering, sintered glass, artificial bone, or a combination thereof.

In use, the heads 66 articulate with the superior halves of the left and right facet joints with the next adjacent vertebra level. As earlier described with reference to the single link structures, the superior halves of the facet joints can comprise the natural superior articular process 22 itself, or it can comprise a prosthetic facet created, e.g., by the cups 64 of another link assembly 56 secured to the next adjacent lower vertebra.

The interlocking of the criss-crossing link bodies 58 and 56 increases the strength of the overall link assembly 56. The link assembly 56 distributes forces to both of the pedicles (and the spinous process, if desired), rather than relying upon fixation to a single pedicle.

Like the link 26', the link assembly 56 is well suited for implantation in procedures requiring replacement of multiple levels of facet joints, and can be interlinked in superior and inferior pairs, like a structure formed out of interlinking tinker-toy pieces. Like the link 26', the link assembly 56 also allows subsequent surgeries to build upon already replaced levels, rather than requiring the removal and replacement of an existing implant to accommodate replacement of failing facet joints in an adjacent level.

The size and shape of any prosthesis disclosed herein are desirably selected by the physician, taking into account the morphology and geometry of the site to be treated. The shape of the joint, the bones and soft tissues involved, and the local structures that could be harmed if move inappropriately, are generally understood by medical professionals using textbooks of human anatomy along with their knowledge of the site and its disease and/or injury. The physician is also desirably able to select the desired shape and size of the prosthesis and its placement in and/or around the joint based upon prior analysis of the morphology of the targeted joint using, for example, plain film x-ray, fluoroscopic x-ray, or MRI or CT scanning. The shape, size and placement are desirably selected to optimize the strength and ultimate bonding of the prosthesis to the surrounding bone and/or tissue of the joint.

Other embodiments and uses of the invention will be apparent to those skilled in the art from consideration of the specification and practice of the invention disclosed herein. All documents referenced herein are specifically and entirely incorporated by reference. The specification and examples should be considered exemplary only with the true scope and spirit of the invention indicated by the following claims. As will be easily understood by those of ordinary skill in the art, variations and modifications of each of the disclosed embodiments can be easily made within the scope of this invention as defined by the following claims.

I claim:

1. A prosthesis assembly to replace all or a portion of a caudal portion of a left natural facet joint and all or a portion of a caudal portion of a right natural facet joint on a vertebral body, the prosthesis assembly comprising:
    a left prosthesis body accommodating fixation to the vertebral body at or near a left pedicle and without support by a lamina,
    an artificial left facet joint structure carried by the left prosthesis body adapted and configured to replace all or a portion of a caudal portion of the left natural facet joint,
    a right prosthesis body accommodating fixation to the vertebral body at or near a right pedicle and without support by a lamina, and
    an artificial right facet joint structure carried by the right prosthesis body adapted and configured to replace all or a portion of a caudal portion of the right natural facet joint.

2. A prosthesis assembly according to claim 1 wherein at least one of the artificial left and right facet joint structures is adapted and configured to replace a natural articular process of a caudal portion of the respective one of the left and right natural facet joints.

3. A prosthesis assembly according to claim 1 wherein at least one of the artificial left and right facet joint structures is adapted and configured to replace a natural articular process of a caudal portion of the respective one of the left and right natural facet joints after removal of at least some of a lamina from the vertebral body.

4. A prosthesis assembly according to claim 1 wherein at least one of the artificial left and right facet joint structures is adapted and configured to replace a natural articular process of a caudal portion of the respective one of the left and right natural facet joints after removal of at least part of a mamillary process from the vertebral body.

5. A prosthesis assembly according to claim 1 wherein at least one of the artificial left and right facet joint structures is adapted and configured to replace a natural articular process of a caudal portion of the respective one of the left and right natural facet joints after removal of at least part of a transverse process from the vertebral body.

6. A prosthesis assembly according to claim 1 wherein at least one of the artificial left and right facet joint structures is adapted and configured to replace a natural articular process of a caudal portion of the respective one of the left and right natural facet joints after removal of at least part of a pedicle from the vertebral body.

7. A prosthesis assembly according to claim 1 wherein at least one of the artificial left and right facet joint structures is adapted and configured to replace a natural articular process of a caudal portion of the respective one of the left and right natural facet joints after removal of at least some of the natural articular process from the vertebral body.

8. A prosthesis assembly according to claim 1 wherein at least one of the artificial left and right facet joint structures is adapted and configured to replace a natural articular process of a caudal portion of the respective one of the left and right natural facet joints after removal of at least some of the natural articular process and of at least some of a lamina from the vertebral body.

9. A prosthesis assembly according to claim 1 wherein at least one of the artificial left and right facet joint structures is adapted and configured to replace a natural articular process of a caudal portion of the respective one of the left and right natural facet joints after removal of at least some of the natural articular process and of at least some of a mamillary process from the vertebral body.

10. A prosthesis assembly according to claim 1 wherein at least one of the artificial left and right facet joint structures is adapted and configured to replace a natural articular process of a caudal portion of the respective one of the left and right natural facet joints after removal of at least some of the natural articular process and of at least part of a transverse process from the vertebral body.

11. A prosthesis assembly according to claim 1 wherein at least one of the artificial left and right facet joint structures is adapted and configured to replace a natural articular process of a caudal portion of the respective one of the natural left and right facet joints after removal of at least some of the natural articular process and of at least part of a pedicle from the vertebral body.

12. A prosthesis assembly according to claim 1 wherein at least one of the artificial left and right facet joint structures is adapted and configured to replace a natural articular process of a caudal portion of the respective one of the left and right natural facet joints, and wherein at least one of the prosthesis bodies is adapted and configured to replace at least some of a lamina of the vertebral body.

13. A prosthesis assembly according to claim 1 wherein at least one of the artificial left and right facet joint structures is adapted and configured to replace a natural articular process of a caudal portion of the respective one of the left and right natural facet joints, and wherein at least one of the prosthesis bodies is adapted and configured to replace at least some of a mamillary process of the vertebral body.

14. A prosthesis assembly according to claim 1 wherein at least one of the artificial left and right facet joint structures is adapted and configured to replace a natural articular process of a caudal portion of the respective one of the left and right natural facet joints, and wherein at least one of the prosthesis bodies is adapted and configured to replace at least some of a pedicle of the vertebral body.

15. A prosthesis assembly according to claim 1 wherein at least one of the prosthesis bodies is adapted and configured to replace at least some of a lamina of the vertebral body.

16. A prosthesis assembly according to claim 1 wherein at least one of the prosthesis bodies is adapted and configured to replace at least some of a mamillary process of the vertebral body.

17. A prosthesis assembly according to claim 1 wherein at least one of the prosthesis bodies is adapted and configured to replace at least some of a pedicle of the vertebral body.

18. A prosthesis assembly according to claim 1 wherein at least one of the artificial left and right facet joint structures is adapted and configured to articulate with a cephalad portion of the respective one of the left and right facet joints of an adjoining vertebral body.

19. A prosthesis assembly according to claim 1 wherein at least one of the artificial left and right facet joint structures is made of at least one selected prosthetic material.

20. A prosthesis according to claim 1 wherein the selected prosthetic material includes polyethylene, rubber, tantalum, titanium, chrome cobalt, surgical steel, bony in-growth material, ceramic, artificial bone, or a combination thereof.

21. A prosthesis assembly according to claim 1 wherein a connecting member joins the left and right prosthesis bodies without support by a lamina.

22. A prosthesis assembly according to claim 1 wherein at least one of the left and right prosthesis bodies includes a fastening element installed within the vertebral body at or near a pedicle to fix the respective prosthesis body to the vertebral body.

23. A prosthesis assembly according to claim 1 wherein at least one of the left and right prosthesis bodies includes a fastening element installed within the vertebral body at or near a pedicle to fix the respective prosthesis body to the vertebral body, and wherein the respective one of the artificial left and right facet joint structures is carried by the fastening element.

24. A prosthesis assembly according to claim 23 wherein the respective one of the artificial facet joint structures is fixed to the fastening element.

25. A prosthesis assembly according to claim 23 wherein the respective one of the artificial facet joint structures is fixed to the fastening element by an adhesive or cement.

26. A prosthesis assembly according to claim 23 wherein the respective one of the artificial facet joint structures is fixed to the fastening element by mechanical attachment.

27. A prosthesis assembly according to claim 23 wherein the respective one of the artificial facet joint structures is removably carried by the fastening element.

28. A prosthesis assembly according to claim 23 wherein the respective one of the artificial facet joint structures is removably attached to the fastening element by frictional engagement.

29. A prosthesis assembly according to claim 23 wherein the respective one of the artificial facet joint structures is removably attached to the fastening element by a Morse taper.

30. A prosthesis assembly according to claim 23 wherein the respective one of the artificial facet joint structures comprises an insert fitted to the fastening element.

31. A prosthesis assembly according to claim 23 wherein the respective one of the artificial facet joint structures comprises an insert fitted by frictional engagement to the fastening element.

32. A prosthesis assembly according to claim 23 wherein the respective one of the artificial facet joint structures comprises an insert fitted by a Morse taper to the fastening element.

33. A prosthesis assembly according to claim 23 wherein the respective one of the artificial facet joint structures comprises a removable insert fitted to the fastening element.

34. A prosthesis assembly according to claim 23 wherein the respective one of the artificial facet joint structures pivots with respect to the fastening element.

35. A prosthesis assembly according to claim 22 wherein the fastening element is fixed to the vertebral body by an adhesive or cement.

36. A prosthesis assembly according to claim 22 wherein the fastening element includes a bony in-growth material.

37. A prosthesis assembly according to claim 22 wherein the fastening element includes a screw installed within the vertebral body at or near a pedicle.

38. A prosthesis assembly according to claim 22 wherein the fastening element includes a stem installed within the vertebral body at or near a pedicle.

39. A prosthesis assembly according to claim 22 wherein the fastening element including means for resisting rotation after installation in the vertebral body.

40. A prosthesis assembly according to claim 1 wherein at least one of the prosthesis bodies is fixed to the vertebral body by an adhesive or cement.

41. A prosthesis assembly according to claim 1 wherein at least one of the prosthesis bodies includes a bony in-growth material.

42. A method of replacing, on a vertebral body, all or a portion of a caudal portion of a left natural facet joint and all or a portion of a caudal portion of a right natural facet joint using the prosthesis assembly defined in claim 1 to provide improved support for the spinal column, the method comprising the steps of
  (i) removing all or a portion of the caudal portions of the left and right natural facet joints from the vertebral body, and
  (ii) fixing the prosthesis assembly as defined in claim 1 to the vertebral body to replace both removed caudal portions of the left and right natural facet joints with the artificial facet joint structure.

43. A method according to claim 42 further including a step of removing at least some of the lamina from the vertebral body.

44. A method according to claim 42 further including a step of removing at least part of a mamillary process from the vertebral body.

45. A method according to claim 42 further including a step of removing at least part of a transverse process from the vertebral body.

46. A method according to claim 42 further including a step of removing at least part of a pedicle from the vertebral body.

47. A prosthesis assembly according to claim 21 wherein at least one of the left and right prosthesis bodies includes a fastening element installed within the vertebral body at or near a pedicle to fix the respective prosthesis body to the vertebral body, and the fastening element is fixed to the vertebral body by an adhesive or cement.

48. A prosthesis assembly according to claim 21 wherein at least one of the left and right prosthesis bodies includes a fastening element installed within the vertebral body at or near a pedicle to fix the respective prosthesis body to the vertebral body, and the fastening element includes a bony in-growth material.

49. A prosthesis assembly according to claim 21 wherein at least one of the left and right prosthesis bodies includes a fastening element installed within the vertebral body at or near a pedicle to fix the respective prosthesis body to the vertebral body, and the fastening element includes a screw installed within the vertebral body at or near a pedicle.

50. A prosthesis assembly according to claim 21 wherein at least one of the left and right prosthesis bodies includes a fastening element installed within the vertebral body at or near a pedicle to fix the respective prosthesis body to the vertebral body, and the fastening element includes a stem installed within the vertebral body at or near a pedicle.

51. A prosthesis assembly according to claim 21 wherein at least one of the left and right prosthesis bodies includes a fastening element installed within the vertebral body at or near a pedicle to fix the respective prosthesis body to the vertebral body, and the fastening element includes means for resisting rotation after installation in the vertebral body.

52. A prosthesis assembly according to claim 23 wherein the fastening element is fixed to the vertebral body by an adhesive or cement.

53. A prosthesis assembly according to claim 23 wherein the fastening element includes a bony in-growth material.

54. A prosthesis assembly according to claim 23 wherein the fastening element includes a screw installed within the vertebral body at or near a pedicle.

55. A prosthesis assembly according to claim 23 wherein the fastening element includes a stem installed within the vertebral body at or near a pedicle.

56. A prosthesis assembly according to claim 23 wherein the fastening element including means for resisting rotation after installation in the vertebral body.

* * * * *